US012618093B2

(12) United States Patent
Molina García et al.

(10) Patent No.: US 12,618,093 B2
(45) Date of Patent: May 5, 2026

(54) METHOD, AN ELECTROCHEMICAL SENSOR AND A SYSTEM FOR SELECTIVE DETECTION OF INFECTIONS

(71) Applicants: Universitat Politecnica de Catalunya, Barcelona (ES); B. Braun Surgical, SA, Rubí (ES)

(72) Inventors: Brenda Guadalupe Molina García, Barcelona (ES); Elaine Aparecida Armelin Diggroc, Castellví de Rosanes (ES); Pau Turon Dols, Rubí (ES); Carlos Enrique Alemán Llansó, Castellví de Rosanes (ES)

(73) Assignees: Universitat Politecnica de Catalunya, Barcelona (ES); B. Braun Surgical, SA, Rubí (ES)

( * ) Notice: Subject to any disclaimer, the term of this patent is extended or adjusted under 35 U.S.C. 154(b) by 839 days.

(21) Appl. No.: 17/438,153

(22) PCT Filed: Mar. 11, 2020

(86) PCT No.: PCT/EP2020/056487
§ 371 (c)(1),
(2) Date: Sep. 10, 2021

(87) PCT Pub. No.: WO2020/182872
PCT Pub. Date: Sep. 17, 2020

(65) Prior Publication Data
US 2022/0177942 A1 Jun. 9, 2022

(30) Foreign Application Priority Data
Mar. 12, 2019 (EP) ..................................... 19382178

(51) Int. Cl.
*C12Q 1/00* (2006.01)
*A61B 5/145* (2006.01)
(Continued)

(52) U.S. Cl.
CPC .......... *C12Q 1/008* (2013.01); *A61B 5/14546* (2013.01); *A61B 5/1473* (2013.01); *C12Q 1/02* (2013.01)

(58) Field of Classification Search
CPC ...... C12Q 1/008; C12Q 1/02; A61B 5/14546; A61B 5/1473; A61B 5/1468; A61B 5/263; A61B 5/268; G01N 2800/26
See application file for complete search history.

(56) References Cited

U.S. PATENT DOCUMENTS 8,005,526 B2 8/2011 Martin et al.
2001/0002421 A1 5/2001 Stratton et al.
(Continued)

FOREIGN PATENT DOCUMENTS

EP 2514359 A2 10/2012
JP 2002512622 A 4/2002
(Continued)

OTHER PUBLICATIONS

Rajendran Rajaram, Sukeri Anandhakumar, Jayaraman Mathiyarasu, Electrocatalytic oxidation of NADH at low overpotential using nanoporous poly(3,4)-ethylenedioxythiophene modified glassy carbon electrode, Journal of Electroanalytical Chemistry, vol. 746, 2015, pp. 75-81, ISSN 1572-6657 (Year: 2015).*
(Continued)

*Primary Examiner* — Jason M Sims
*Assistant Examiner* — Kyle W. Kretzer
(74) *Attorney, Agent, or Firm* — Christopher A. Rothe; CM Law

(57) ABSTRACT

A method, an electrochemical sensor and a system for selective detection of infections. The method detects a concentration of nicotinamide adenine dinucleotide, NADH, from a bacterial culture through a cyclic voltammetry or chronoamperometry applied to an electrochemically active
(Continued)

Figure 1:
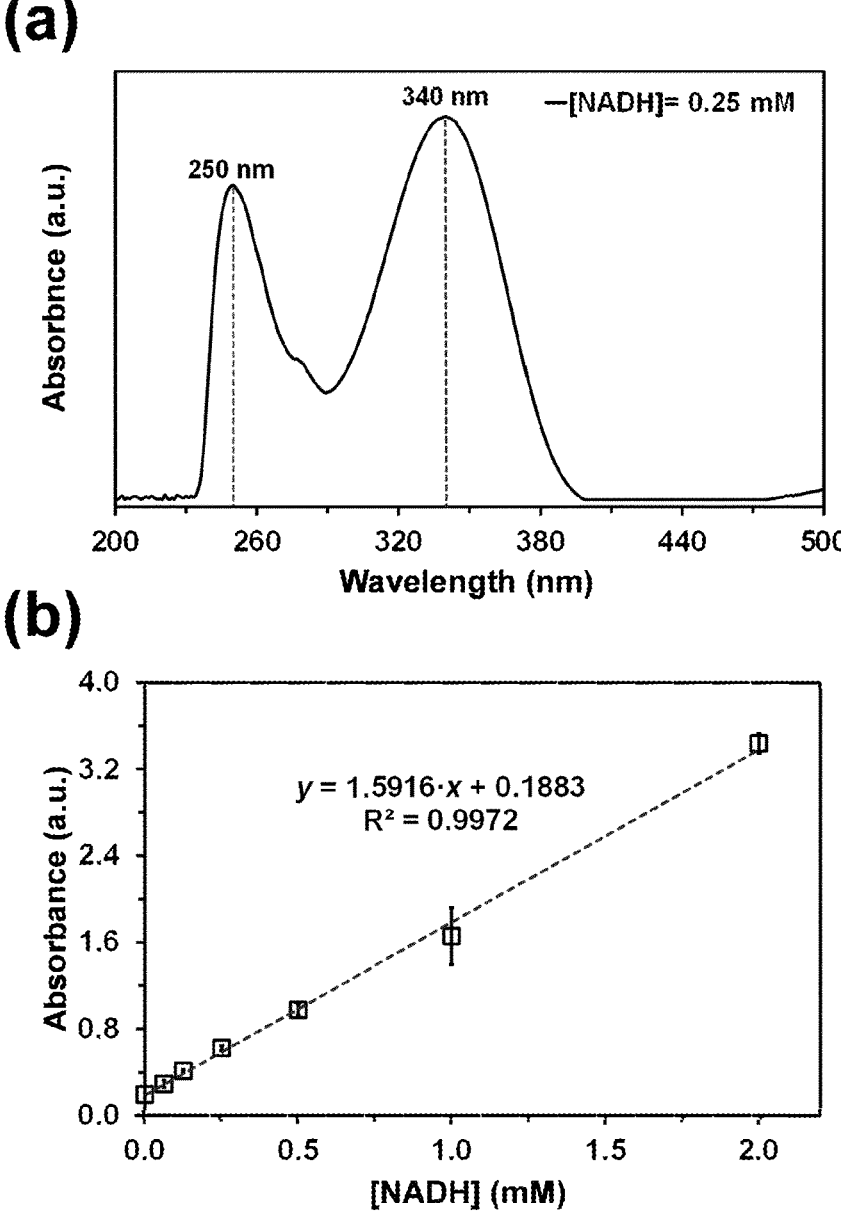

polymer. Therefore, prokaryotic cells can be detected while eukaryotic cells remain undetected. The infections can include bacterial infections and fungi or yeasts microbial infections.

9 Claims, 22 Drawing Sheets

(51) Int. Cl.
A61B 5/1473 (2006.01)
C12Q 1/02 (2006.01)

(56) References Cited

U.S. PATENT DOCUMENTS

| | | | |
|---|---|---|---|
| 2004/0096927 A1 | 5/2004 | Chittock et al. | |
| 2004/0133084 A1* | 7/2004 | Rule | B01L 3/508 |
| | | | 600/310 |
| 2007/0060815 A1* | 3/2007 | Martin | A61B 5/266 |
| | | | 600/372 |
| 2008/0161247 A1 | 7/2008 | Surolia et al. | |
| 2010/0204802 A1* | 8/2010 | Wilson | A61B 5/24 |
| | | | 623/23.6 |
| 2011/0261430 A1* | 10/2011 | Mazurkiewicz | G02F 1/15165 |
| | | | 359/275 |
| 2018/0369587 A1* | 12/2018 | Ludwig | A61B 5/0538 |
| 2019/0134308 A1* | 5/2019 | Newberry | A61M 5/14248 |
| 2020/0190342 A1* | 6/2020 | Abidian | A61N 1/0541 |
| 2021/0315492 A1* | 10/2021 | Najdahmadi | A61B 5/1459 |

FOREIGN PATENT DOCUMENTS

| | | |
|---|---|---|
| JP | 2004508833 A | 3/2004 |
| JP | 2009506836 A | 2/2009 |
| WO | 2009055530 A2 | 4/2009 |
| WO | 2019022469 A1 | 1/2019 |

OTHER PUBLICATIONS

Zhang, Z., Milias-Argeitis, A. & Heinemann, M. Dynamic single-cell NAD(P)H measurement reveals oscillatory metabolism throughout the *E. coli* cell division cycle. Sci Rep 8, 2162 (2018). https://doi.org/10.1038/s41598-018-20550-7 (Year: 2018).*

Molina, Brenda G., et al. "The biocompatible polythiophene-g-polycaprolactone copolymer as an efficient dopamine sensor platform." (2017) Polymer Chemistry 8.39: 6112-6122. (Year: 2017).*

Office Action received in Chinese Application No. 202080035568.0 dated Nov. 28, 2023, with translation, 26 pages.

Balamurugan, et al., "Voltammetric oxidation of NADH at phenyl azo aniline/PEDOT modified electrode," ScienceDirect, Sensors and Actuators B 129 (2008), Sep. 24, 2007, 10 pages.

Manesh, et al., "Electrocatalytic oxidation of NADH at gold nanoparticles loaded poly (3,4-ethylenedioxythiophene)-poly (sty-rene sulfonic acid) film modified electrode and integration of alcohol dehydrogenase for alcohol sensing," ScienceDirect, Talanta 75 (2008), Jan. 21, 2008, 8 pages.

Martin, et al., "In-situ electrochemical analysis of microbial activity," AMB Express, vol. 8, No. 1, Oct. 4, 2018, 10 pages.

Molina, et al., "Electrochemical Sensor for Bacterial Metabolism Based on the Detection of NADH by Polythiophene Nanoparticles," The Journal of Physical Chemistry, vol. 123, No. 36, Aug. 21, 2019, 10 pages.

Rajaram, et al., "Electrocatalytic oxidation of NADH at low overpotential using nanoporous poly (3,4)-ethylenedioxythiophene modified glassy carbon electrode," Journal of Electroanalytical Chemistry, Mar. 24, 2015, 8 pages.

Search Report received in European Application No. EP 19 38 2178 dated Jul. 19, 2019, 7 pages.

Search Report received in International Application No. PCT/EP2020/056487 dated Jun. 17, 2020, 6 pages.

Written Opinion received in International Application No. PCT/EP2020/056487 dated Jun. 17, 2020, 8 pages.

Zhang, et al., "Dynamic single-cell NAD(P)H measurement reveals oscillatory metabolism throughout the *E. coli* cell division cycle," Scientific Reports, Jan. 22, 2018, 10 pages.

* cited by examiner

(a)

(b)

(a)

(b)

METHOD, AN ELECTROCHEMICAL SENSOR AND A SYSTEM FOR SELECTIVE DETECTION OF INFECTIONS

CROSS-REFERENCE TO RELATED APPLICATIONS

This application is the United States national phase entry of International Application No. PCT/EP2020/056487, filed Mar. 11, 2020, and claims the benefit of priority of German Application No. 19382178.2, filed Mar. 12, 2019. The contents of International Application No. PCT/EP2020/056487 and German Application No. 19382178.2 are incorporated by reference herein in their entireties.

FIELD

The present invention is directed, in general, to the field of electrochemical detection of prokaryotic cells. In particular, the invention relates to a method, to an electrochemical sensor and to a system for selective detection of bacteria, among other prokaryotic microbial agents such as fungi and yeasts.

BACKGROUND

Bacteria embed themselves in a hydrated extracellular matrix of polysaccharides and proteins, forming a slimy layer known as a biofilm. Biofilms, which are considered as an adaptation of microbes to hostile environments, are generated after initial adhesion of bacteria onto any kind of living or inert surface and their subsequent immobilization growth and reproduction. During the growth phase, bacteria produce extracellular biopolymers that extend developing a complex framework of molecular fibers with unique characteristics, the most important one being its capacity to hinder the access of antimicrobials through it. As a consequence, the adhered microorganisms increase their antimicrobial resistance, becoming up to one thousand times more resistant to antibiotics.

In the biomedical field, bacterial biofilm infections, which are typically associated with patients with indwelling devices for the purpose of medical treatments, attract significant clinical investigations since once established, it becomes difficult to eradicate. Thus, with the progress of medical sciences, the application of medical prostheses and/or artificial organs in the treatment of human diseases is experiencing an exponential growth and, therefore, bacterial biofilm infections become more frequent. Unfortunately, the vast majority of internal (e.g. vascular prosthesis, cerebrospinal fluid shunts, prosthetic heart valves and breast implants) and external (e.g. dentures and contact lenses) prostheses, as well as hip prosthesis (i.e. when hip joints are replaced by prosthetic implants) may result in biofilm infections. Strategies for prevention of biofilm infections become therefore challenging and attract significant attention.

One of the emerging methods for biofilm detection is the use of electrochemical impedance spectroscopy (EIS) measures employing polymeric sensors. In EIS, the electrochemical impedance across the electrode-electrolyte interface is carried out over a wide range of frequencies to elicit information about the properties of the interface. In the case of biofilms, successful detection is based on changes related to charge transfer resistance and capacitance corresponding to the maturing stages of biofilm development. However, analysis of the electrical behavior of the development of biofilms is not a simple task and development of simpler or more selective methods is highly desirable.

Apart from that, eukaryotic cells present two major nicotinamide adenine dinucleotide (NAD) pools, the cytosolic and the mitochondrial pools. Although aerobic respiration reactions in eukaryotic cells take place in the mitochondria, the mitochondrial and cytosolic NAD ratio is cell-type specific. However, a distinctive characteristic of eukaryotic cells is that mitochondrial double-membrane is impermeable to reduced NAD (NADH) and oxidized NAD (NAD+), i.e. the outer membrane is quite permeable but the inner membrane is highly folded into cristae. As a consequence, the mitochondrial NAD levels are maintained even upon massive depletion of cytosolic NAD occurs. In opposition, as prokaryotes' do not have mitochondria, their whole respiration occurs in the cytosol or on the inner surfaces of the cells membrane. Therefore, as prokaryotic cellular membranes are permeable to NAD, the extracellular detection of NAD could be an appropriated approach for detecting the presence of bacteria in a eukaryotic cell environment, and as a result, to selectively identify growing bacterial infections on an implanted medical device.

Thus, there is a need of: a) identify appropriated bacteria markers (i.e. chemicals with redox properties) for electrochemical detection related to microbial infections, and in particular of biofilm formation; and b) integrate electrochemical sensors for such bacteria markers into prosthetic and implantable materials.

Several developments in this field have yielded electrochemical sensors for NADH. For example, in "*Electrocatalytic oxidation of NADH at low overpotential using nanoporous poly(3,4)-ethylenedioxythiophene modified glassy carbon electrode*", Rajendran Rajaram et al. authors developed a conducting polymer (PEDOT) sensor for NADH against fouling. Unlike present invention, however, no connection between the concentration of NADH in a biological fluid and the microbial infection is mentioned or even insinuated in this work. Likewise, in "*Electrocatalytic oxidation of NADH at gold nanoparticles loaded poly(3,4-ethylenedioxythiophene)-poly(styrene sulfonic acid) film modified electrode and integration of alcohol dehydrogenase for alcohol sensing*", Manesh K. M. et al. authors developed a sensor to detect NADH as cofactor for enzymatic reactions. No relation was stablished between the NADH concentration in a biological fluid and the level of microbial infection. In "*Voltammetric oxidation of NADH at phenyl azo aniline/PEDOT modified electrode*", Balamurugan et al. a conducting polymer (PEDOT)-based sensor is developed to detect NADH as substrate for deshydrogenase enzymes. Again, no relationship between the metabolism of bacteria and NADH concentration, which is the object of present invention, is mentioned or even imagined in this work.

Finally, EP2514359-A2 refers to conducting polymer-based electrodes as sensors for biomolecules in biological fluids. This patent application neither contains any description about the relationship between NADH concentration and infection. On the contrary, present invention detects the presence and content of bacteria by analyzing the concentration of NADH in the medium, which comes from bacteria metabolism. Indeed, this patent application does not mention NADH among the biomolecules of interest since NADH is not associated to any pathology.

Hence, none of the existing solutions relates the presence of NADH with bacterial infection or other prokaryotic microbial agents, as for example fungi and yeasts.

SUMMARY

Present invention is based on the fact that bacteria membranes are permeable to NADH produced in bacteria respiration reactions and a detectable gradient concentration of NADH is assumed to be obtained in bacteria surrounding environment. Both the presence of extracellular NADH coming from bacteria respiration and the increment of such NADH concentration with bacteria growth have not been disclosed yet. This relationship can be used to control bacterial infection in prosthesis and implants. The utilization of NADH as bacteria marker can allow distinguishing the bacterial growth, and the consequent formation of biofilm, from the growth of eukaryotic cells through a voltammetric or chronoamperometric detection of NAD (i.e. oxidation from NADH to NAD+) using materials, preferably non-toxic and biocompatible, which can be integrated into existing medical devices becoming a new generation of smart biomedical devices.

Present invention evidences the direct relationship between bacterial colonization and the detection of extracellular NADH in the culture medium as well as the increase of the NADH content with the bacteria growth.

Present invention can be extended to other prokaryotic microbial agents involving NADH from respiration reactions, as for example fungi and yeasts. Moreover, present invention can be integrated into other devices for example air or water filters to detect the presence of bacterial infections.

Embodiments of the present invention provide, according to a first aspect, a method for selective detection of infections. The method involves detecting a concentration of NADH from a bacterial culture through a cyclic voltammetry or chronoamperometry applied to an electrochemically active polymer; the infections involving bacterial infections and/or fungi or yeasts microbial infections. Thus, the method allows to detect the prokaryotic cells while it is not responsive against eukaryotic cells. Furthermore, the relationship between the bacterial/microbial infections and the concentration of NADH in the medium is demonstrated.

Embodiments of the present invention also provide, according to a second aspect, an electrochemical sensor for selective detection of infections by identifying NADH from bacteria or microbial agents involving NADH from respiration reactions. The proposed electrochemical sensor comprises a solid substrate (e.g. a film, a mesh, a suture or a three-dimensional device, among others) acting as support; and an electrochemically active polymer deposited on top of the cited support and configured to be electrochemically activated by an (small) electrical potential obtained through a cyclic voltammetry or chronoamperometry.

In use, the electrochemical sensor is adapted to be placed over the surface, or to form part of the surface or integrated in their body, of a medical device such as an internal prosthesis (e.g. vascular prosthesis, cerebrospinal fluid shunts, prosthetic heart valves and breast implants); external prosthesis (e.g. dentures and contact lenses), as well as hip prosthesis; and any kind of implant. Likewise, the medical device in use can be located in or over a bacterial culture or alternatively can be implanted in a living tissue. Furthermore, the electrochemical sensor can be adapted to be placed over the surface or integrated in the body of other devices such as air or water filters. As a result of said electrical potential, the electrochemically active polymer is configured to detect NADH, coming from the metabolism of the bacteria, through oxidation of the NADH molecules into NAD+.

Particularly, the solid substrate is made of a non-toxic and biocompatible material. For example, the solid substrate can be made of polypropylene, polyesters, polyamides, polycarbonates, vitreous carbon, hydroxyapatite or even a metal (such as platinum, gold, stainless steel, titanium, or magnesium alloys).

According to the invention, the electrochemically active polymer can be in the form of particles and/or in the form of an electropolymerized film. Alternatively, the electrochemically active polymer can be in the form of a thread or any other format. In either case, the electrochemically active polymer may comprise polythiophene derivatives particles or films, such as those made of poly(3,4-ethylendioxythiophene), which consists of polythiophene bearing a fused dioxane ring; poly(3,4-ethylendioxythiophene derivatives particles or films, such as poly(hydroxymethyl-3,4-ethylendioxythiophene; or polythiophenes substituted at the 3-position of the thiophene ring.

Embodiments of the present invention also provide, according to a third aspect, a system for selective detection of infections such as bacterial and/or fungi or yeasts infections, comprising a device; an electrochemical sensor; and means (or a unit, element, module) to apply an electrical potential to the electrochemical sensor obtained through a cyclic voltammetry or chronoamperometry. The device can comprise a medical device or an air or water filter.

The electrochemical sensor particularly includes a free-standing solid substrate acting as a support, and an electrochemically active polymer deposited on top of said support and configured to be electrochemically activated. In use, the electrochemical sensor is adapted to be placed over the surface, part of the surface or in the body of said device located in or over a bacterial culture or implanted in a living tissue. Even, the electrochemical sensor could be adapted to be placed on the inside of the device, communicating through channels with the outside. As a result of a cyclic voltammetry or chronoamperometry applied to the electrochemically active polymer, the latter can detect NADH.

According to the proposed system, said means (or unit, element, module) comprises a plurality of electrodes including screen printed electrodes (SPEs) or implantable electrodes, among others. Even, said means can include a wireless signal.

In an embodiment, the medical device comprises internal prosthesis and implants including sutures, surgical meshes, vascular prosthesis, cerebrospinal fluid shunts, prosthetic heart valves and breast implants; external prosthesis including dentures and contact lenses prosthesis; or hip and knee prosthesis.

Thus, present invention uses a simple voltammetry or a chronoamperometry to detect NAD/NAD+ molecules, which come from cells metabolism in a bacterial infection and/or fungi or yeasts microbial infections. In cyclic voltammetry, the response against a (small) linear potential ramp (the initial and final potentials are identical and the cycle reverses at the reversal potential) is recorded by measuring the resulting current, to selectively detect the growth of bacteria. Differential pulse voltammetry (DPV) is another voltammetric method where the current is measured as a function of the potential between the working and the reference electrodes, which is applied as a series of regular voltage pulses superimposed on the potential linear sweep or stair-steps. In chronoamperometry, the potential of the working electrode is stepped and the resulting current from faradaic processes is monitored. The invention is focused in NAD detection, as this biomolecule plays an important role not only as cofactor for numerous deshydrogenase enzymes but also in the electron transfer chain in living organisms. Thus, NAD mediates many redox reactions in its reduced (NADH) and oxidized (NAD+) forms, providing the major source of ATP for aerobic organisms. In addition to energy metabolism of living cells, NADH/NAD+ are closely associated with many pathological states, such as aging, diabetes, cancer and neurological diseases. Bacterial growth has been found to cause the increment of NAD in the culture medium. The electrochemically active polymer acts as immobilized redox mediators, reducing the overpotential for NADH oxidation, accelerating the interfacial electron transfer between NADH and the electrode's surface, and minimizing the presence of competing reactions.

The proposed electrochemical sensor, which can be produced at low cost, could be of clinical benefit in a number of infection monitoring scenarios, where there is a need to differentiate the growth of pathogenic bacteria from eukaryotic cells. Eukaryoric cells should colonize the implant in order to become correctly integrated in the surrounding tissue. The presence of bacteria might hinder the correct healing process and result in a second intervention to remove the infected part. Therefore, the need of detecting a biofilm in an early stage is of outmost interest in order to fight the infection before the mature biofilm is built. On the other hand, some biofilm infections appear after some months after implantation. In this case, the early detection of bacteria colonizing the surgical implant is again of outmost interest in order to protect the health of the patient, giving the opportunity to treat the infection before it becomes a fully mature biofilm that requires a long, risky and costly treatment that can threaten the life of the patient.

BRIEF DESCRIPTION OF THE DRAWING FIGURES

The previous and other advantages and features will be better understood from the following detailed description of embodiments, with reference to the attached figures, which must be considered in an illustrative and non-limiting manner, the figures described as follows:

FIG. 1: (a) UV-Vis spectrum of a 0.025 mM NADH solution in DMEM high glucose supplemented with 2% FBS (pH 8.1) and 0.2% $NaHCO_3$. (b) Calibration curve obtained by representing the absorbance at $\lambda$=340 nm vs. the concentration of NADH (from 0 to 2 mM) added to DMEM high glucose supplemented with 2% FBS (pH 8.1) and 0.2% $NaHCO_3$.

Figure 2:
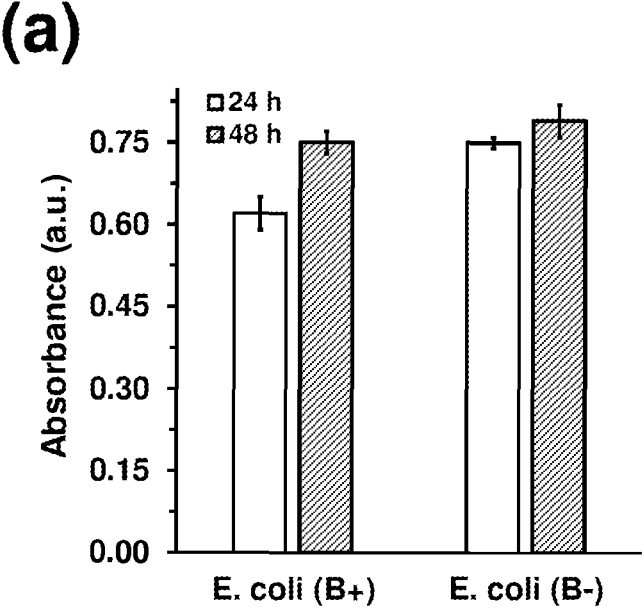
Figure 2:
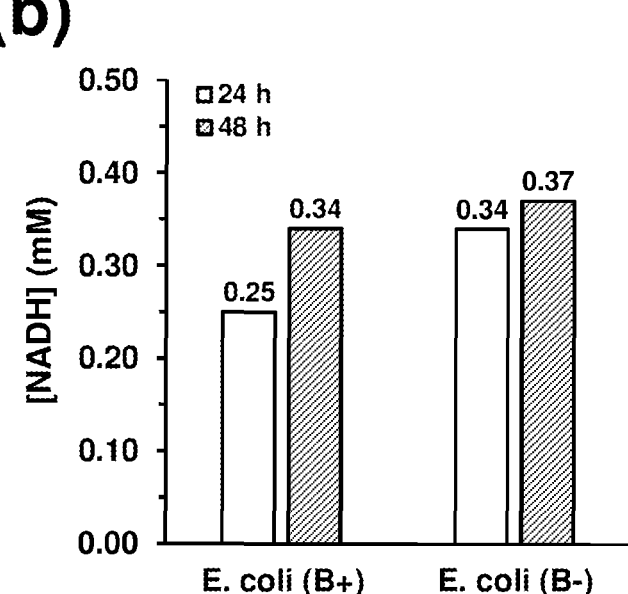

FIG. 2: (a) Absorbance at $\lambda$=340 nm for B+ and B− *E. coli* cultures after 24 and 48 h. (b) NADH concentration in B+ and B− *E. coli* cultures after 24 and 48 h as estimated by applying the calibration curve shown in FIG. 1(*b*).

Figure 3:
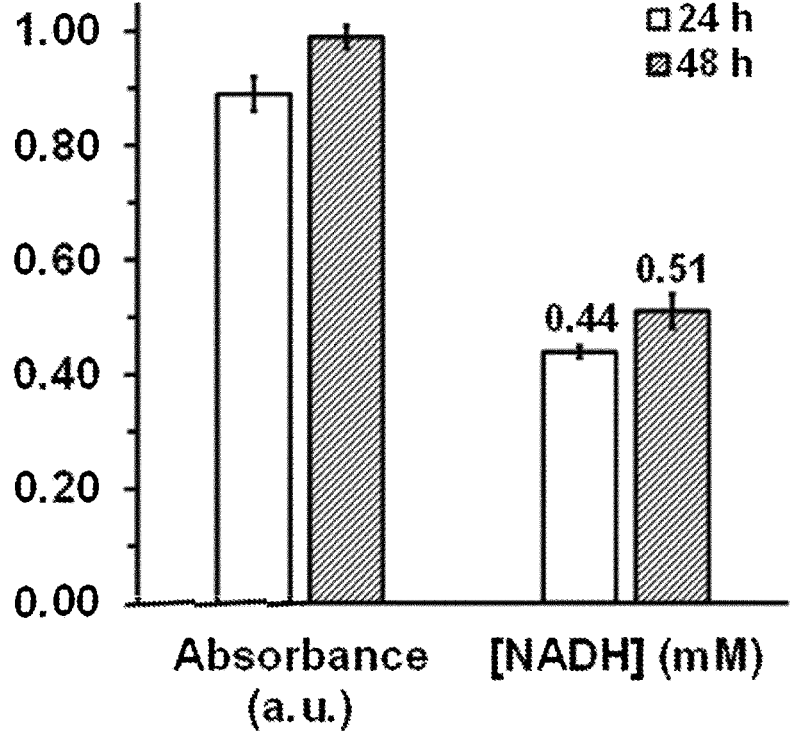

FIG. 3: Absorbance at $\lambda$=340 nm for *S. aureus* cultures after 24 and 48 h and NADH concentration as estimated by applying the calibration curve shown in FIG. 1(*b*).

Figure 4:
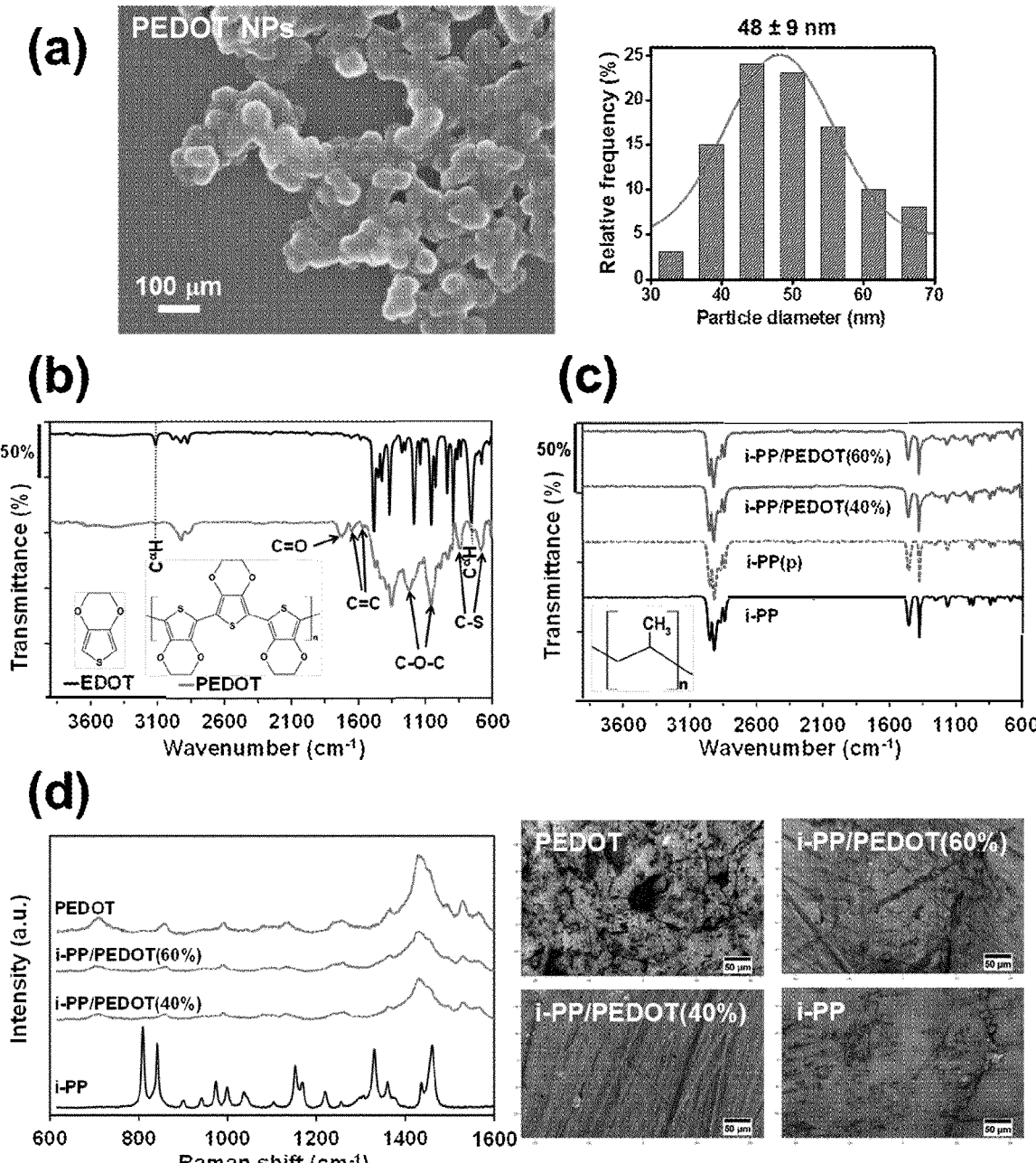

FIG. 4: (a) SEM micrograph of PEDOT nanoparticles (left) and effective diameter histogram derived from SEM measurements (right). (b) FTIR spectra of EDOT monomer and PEDOT nanoparticles. (c) FTIR spectra of neat i-PP, i-PP(p), i-PP/PEDOT(40%) and i-PP/PEDOT(60%) films. (d) Raman spectra (left) and optical micrographs recorded with the Raman microscope (right) of PEDOT nanoparticles and i-PP, i-PP/PEDOT(40%) and i-PP/PEDOT(60%) films.

Figure 5:
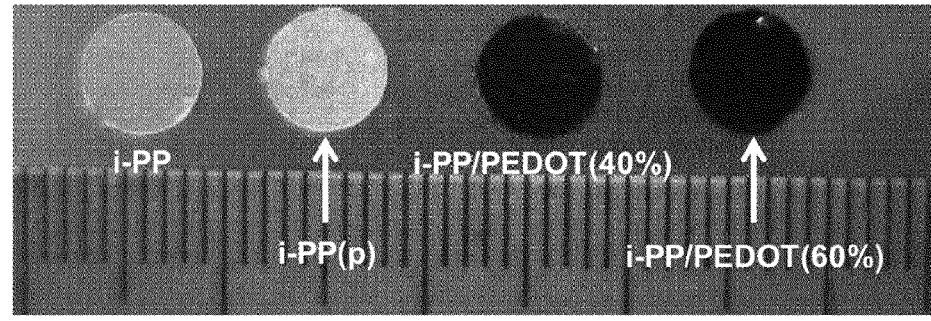
Figure 5:
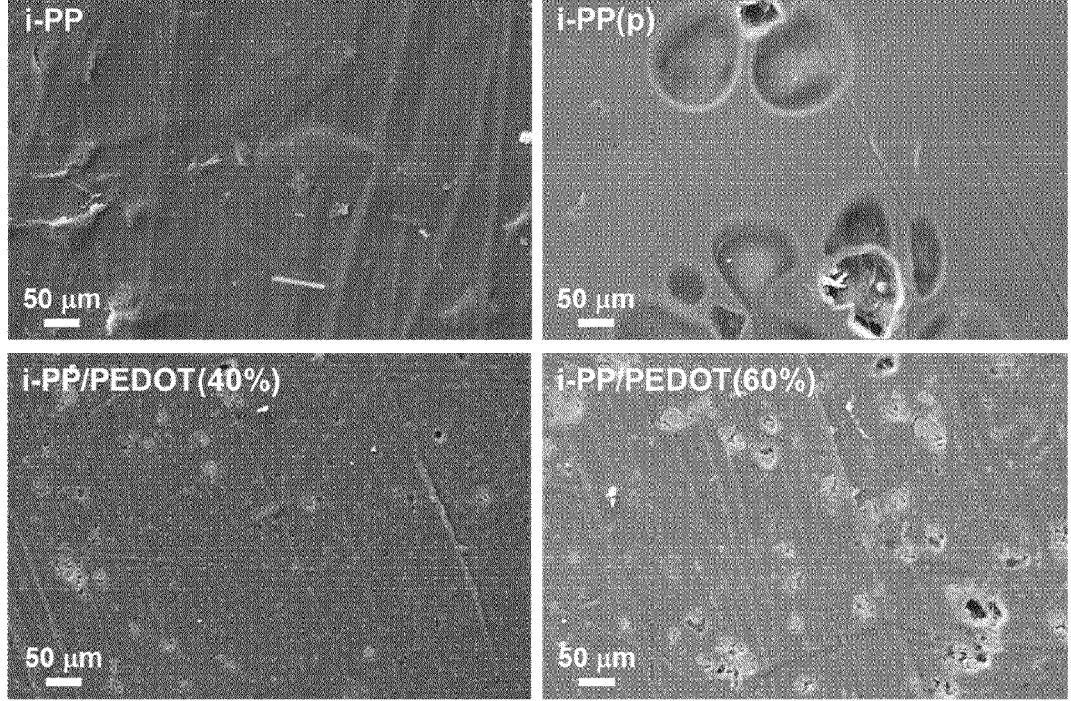

FIG. 5: Photographs (top) and SEM micrographs of i-PP, i-PP(p), i-PP/PEDOT(40%) and i-PP/PEDOT(60%) films. The light spots observed in i-PP/PEDOT films correspond to micro-aggregates of PEDOT nanoparticles.

Figure 6:
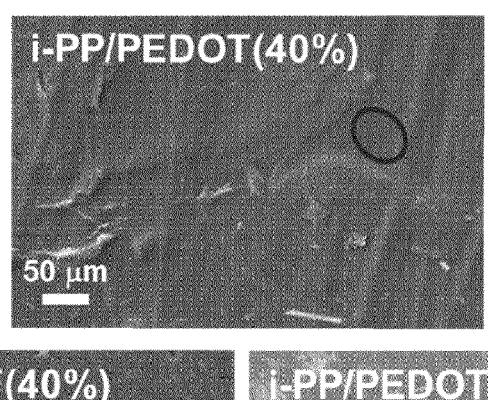
Figure 6:
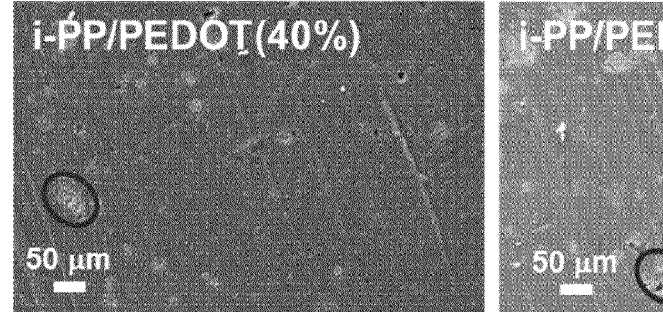
Figure 6:
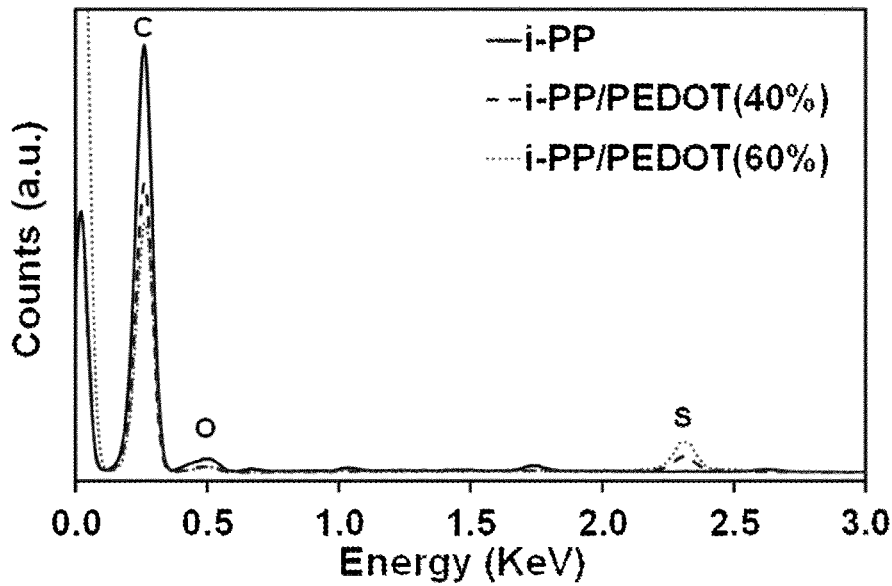

FIG. 6: EDX analysis of neat i-PP and both i-PP/PEDOT (40%) and i-PP/PEDOT(60%) composites. The analyses of films correspond to the regions marked by red circles in SEM micrographs. The presence of sulfur indicates that light spots observed in i-PP/PEDOT films correspond to micro-aggregates of PEDOT NPs.

Figure 7:
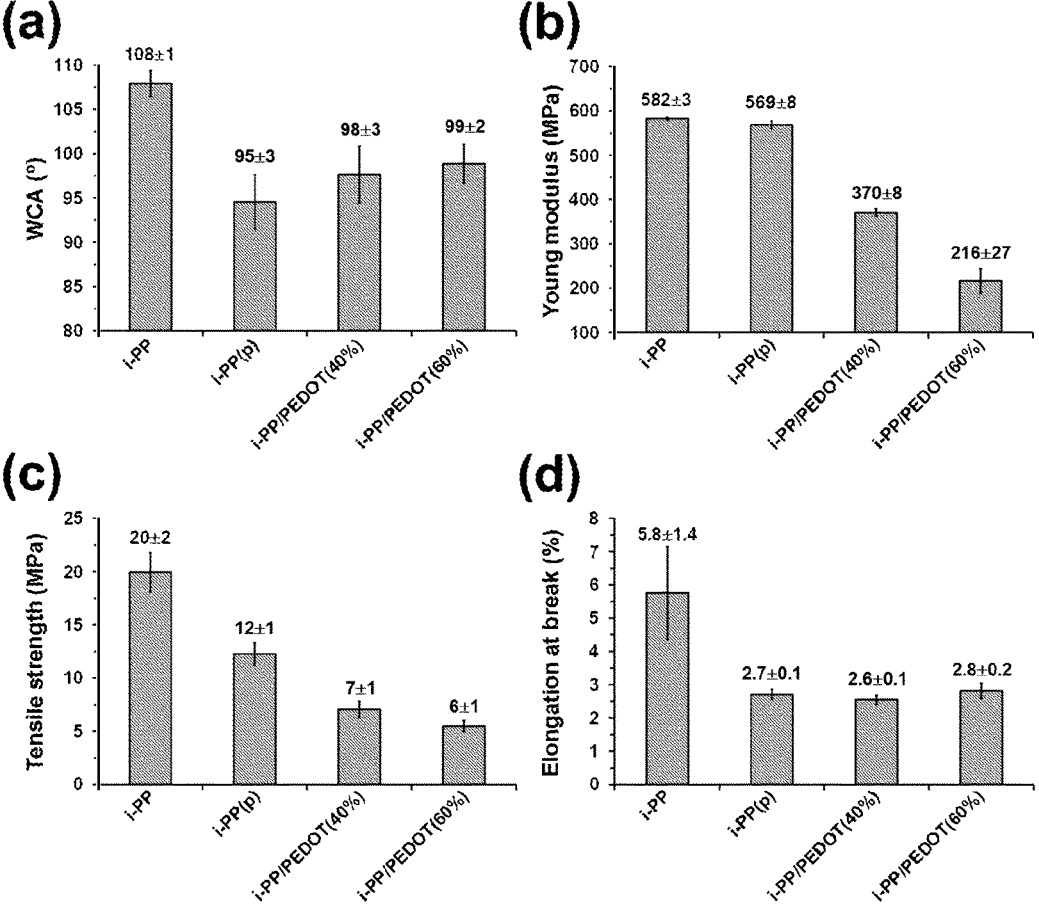

FIG. 7: Comparison of the (a) water contact angle (WCA), (b) Young modulus, (c) tensile strength and (d) elongation at break of i-PP, i-PP(p), i-PP/PEDOT(40%) and i-PP/PEDOT(60%) films.

Figure 8:
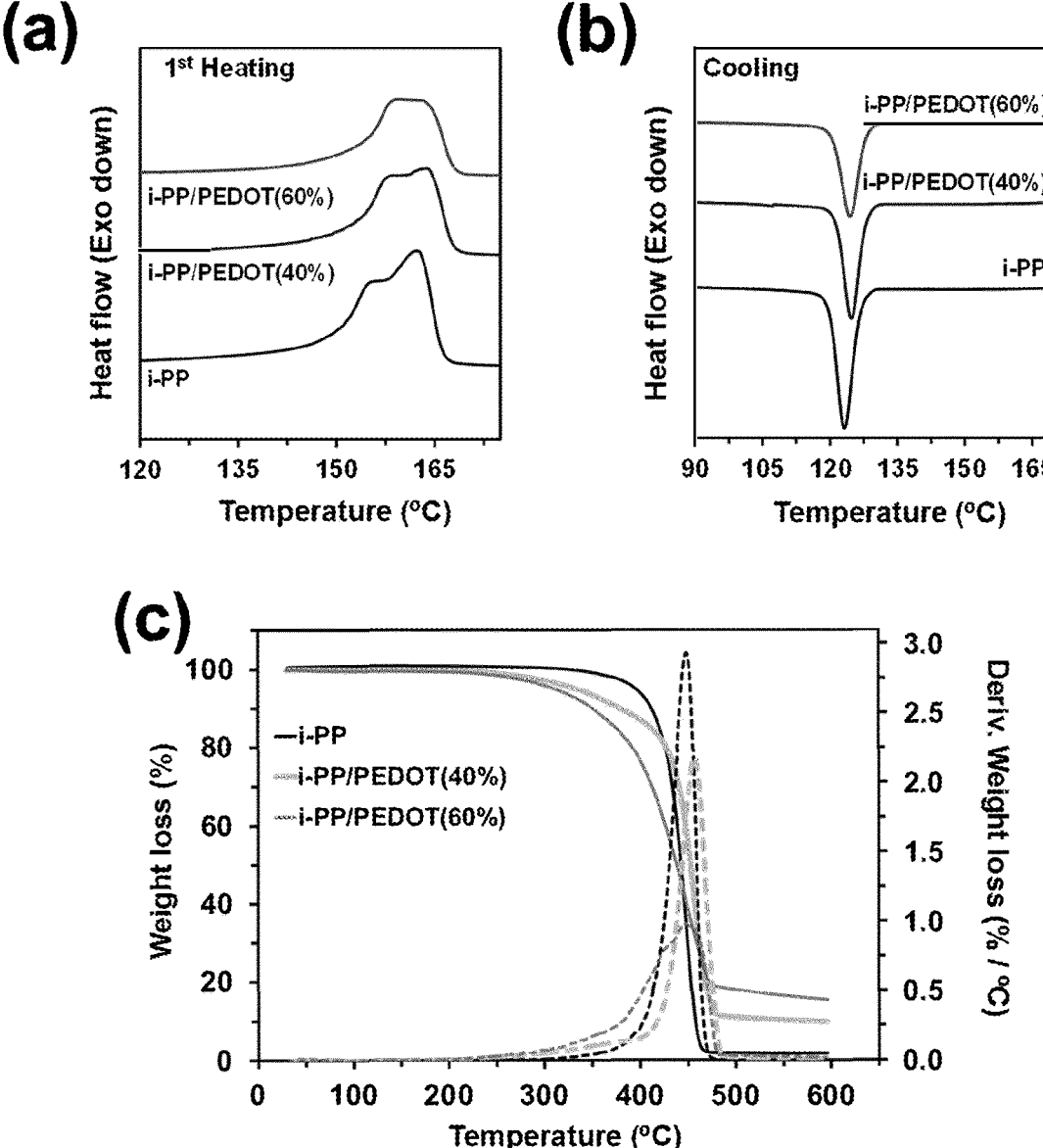

FIG. 8: For neat i-PP and both i-PP/PEDOT(40%) and i-PP/PEDOT(60%) composites: selected regions of the DSC thermograms portraying the (a) melting and the (b) crystallization; (c) TGA and DGTA curves obtained at a heating rate of 10° C./min.

Figure 9:
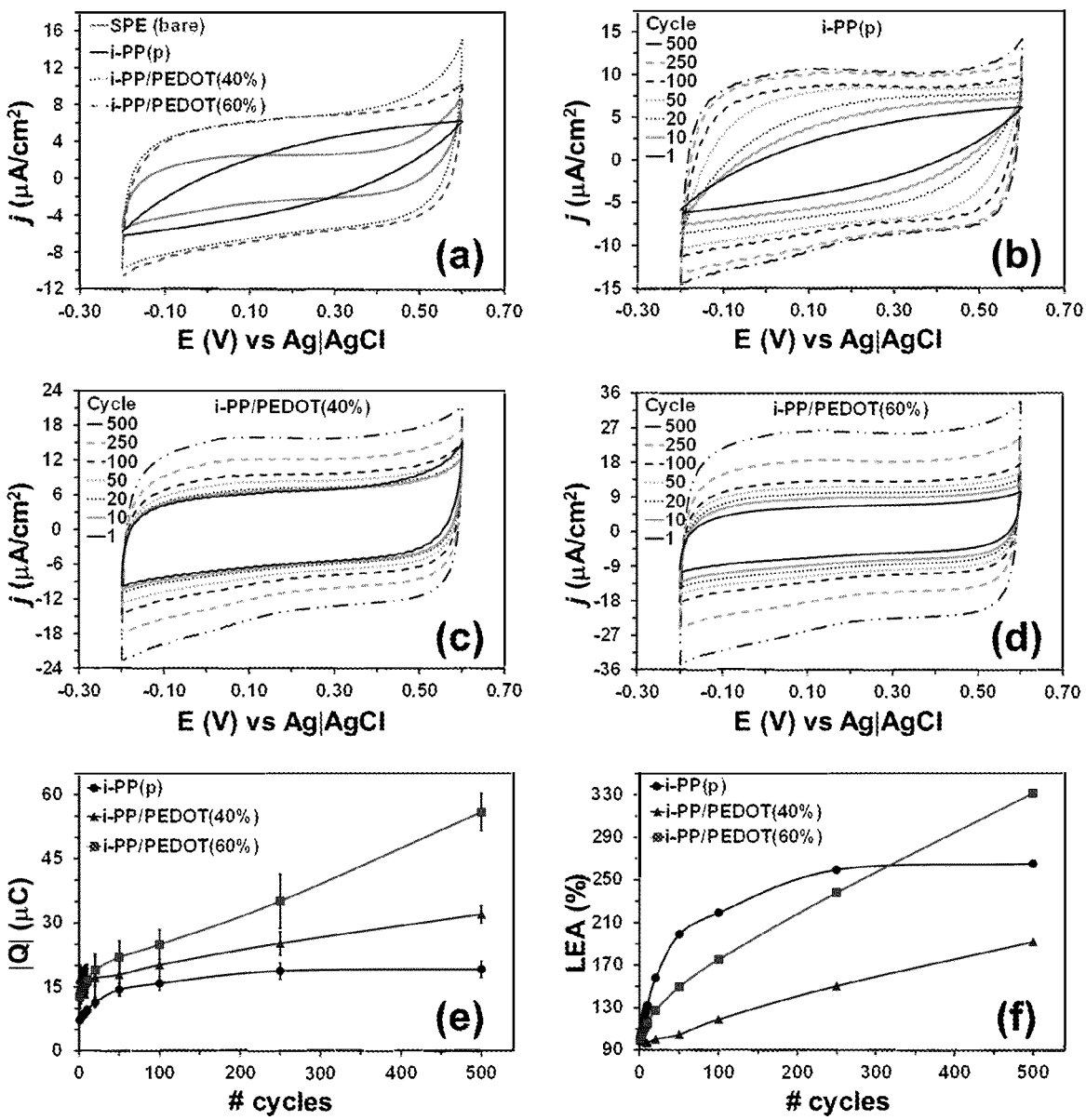

FIG. 9: (a) Control voltammograms of bare and modified SPEs. The latter were obtained by assembling i-PP(p), i-PP/PEDOT(40%) or i-PP/PEDOT(60%) films onto the surface of the SPEs using gelatin as intermediate layer. Cyclic voltammograms recorded after a variable number of consecutive oxidation-reduction cycles: (b) i-PP(p), (c) i-PP/PEDOT(40%) and (d) i-PP/PEDOT(60%). Variation of (e) the measured voltammetric charge (IQI) and (f) the loss of electrochemical activity (LEA) against the number of consecutive redox cycles for i-PP(p), i-PP/PEDOT(40%) and i-PP/PEDOT(60%).

Figure 10:
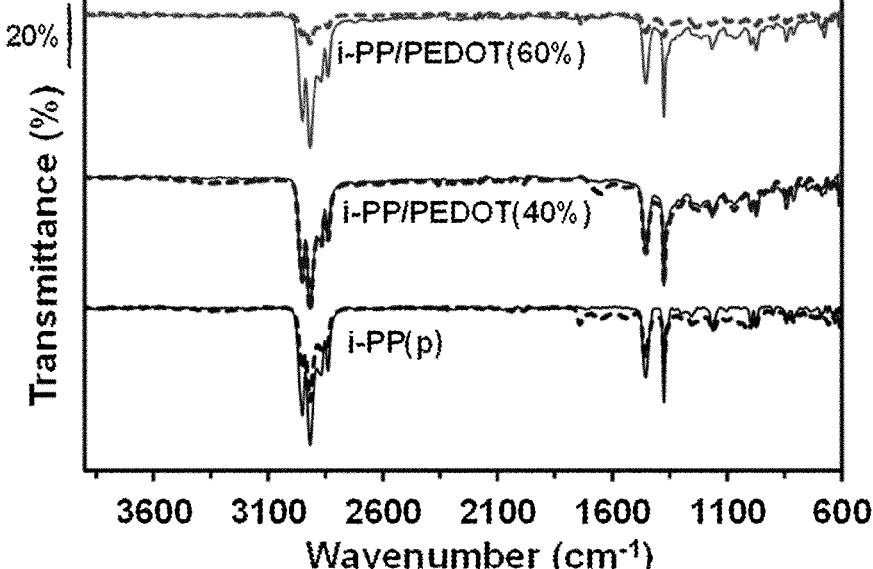

FIG. 10: FTIR spectra of i-PP(p), i-PP/PEDOT(40%) and i-PP/PEDOT(60%) films before (thin solid lines) and after 500 consecutive redox cycles (thick dashed lines).

Figure 11:
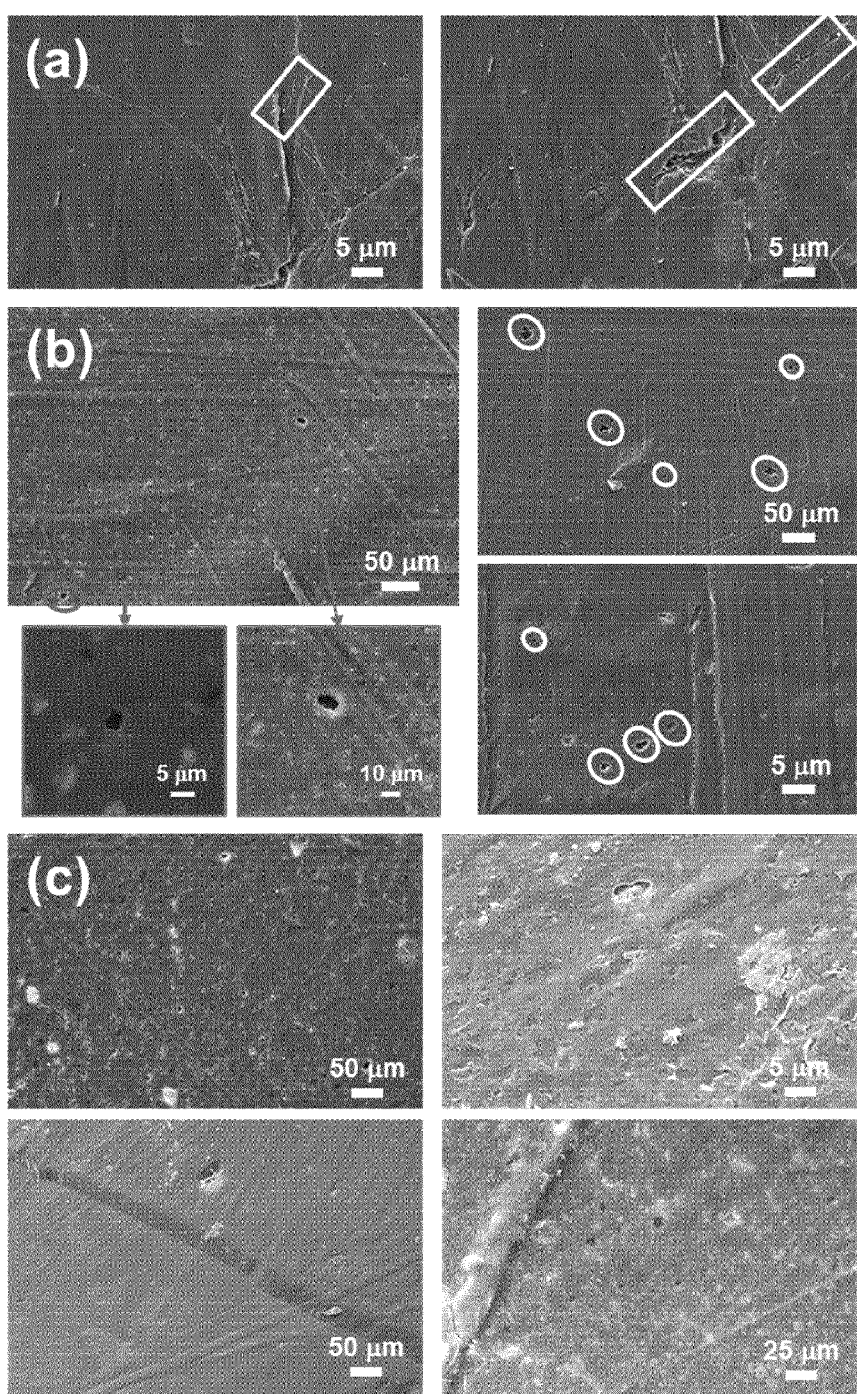

FIG. 11: SEM micrographs of (a) i-PP(p), (b) i-PP/PEDOT(40%) and (c) i-PP/PEDOT(60%) after 500 consecutive redox cycles. Microfractures in i-PP(p) films (marked with rectangles) and pores in i-PP/PEDOT(40%) (marked with circles) are induced by the stress associated to consecutive potential scans. The shape and size of the pores in i-PP/PEDOT(60%) are similar to those of the pores marked in (b).

Figure 12:
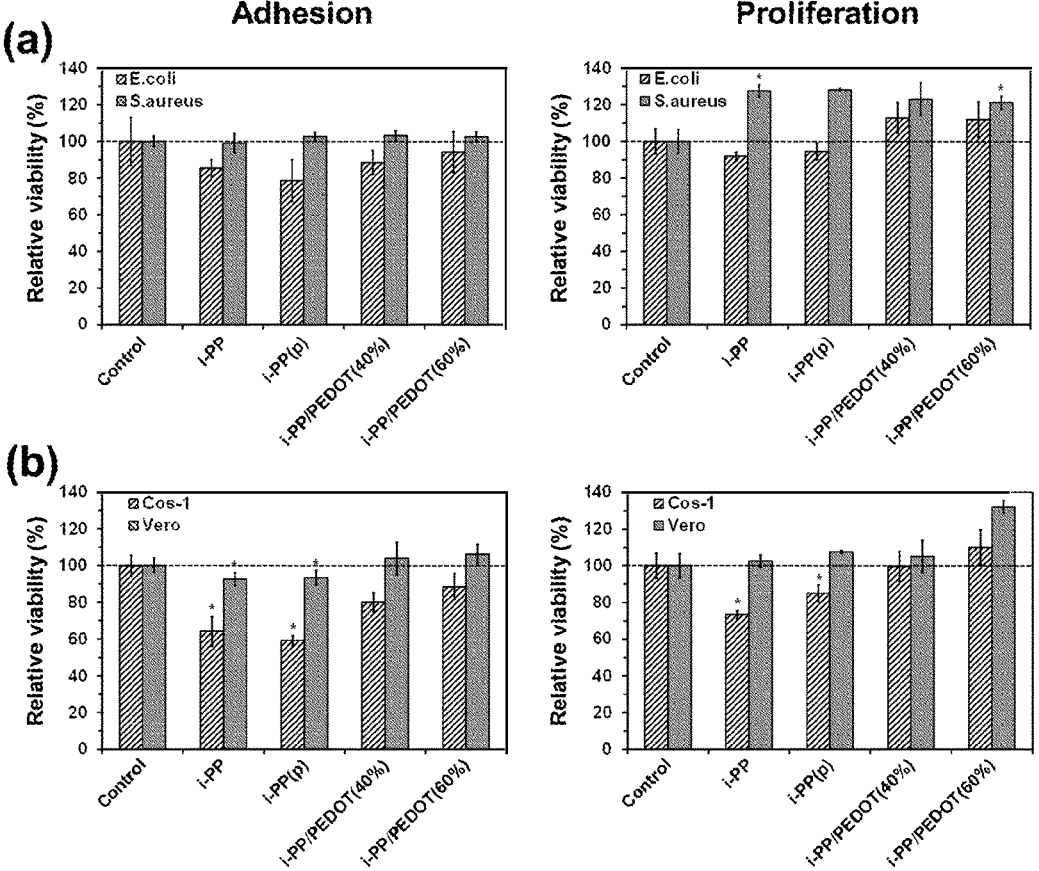

FIG. 12: Cellular adhesion (left) and cellular proliferation (right) on i-PP, i-PP(p), i-PP/PEDOT(40%), i-PP/PEDOT (60%) films. Assays were performed using (a) two representative bacteria (*E. coli* and *S. aureus*) and (*b*) two representative eukaryotic cells (Cos-1 and Vero). Three samples were analyzed for each group. Bars represent the mean standard deviation. The relative viability was established in relation to the control (100%). The asterisk (*) indicates a significant difference with the control, Tukey's test (p<0.03).

Figure 13:
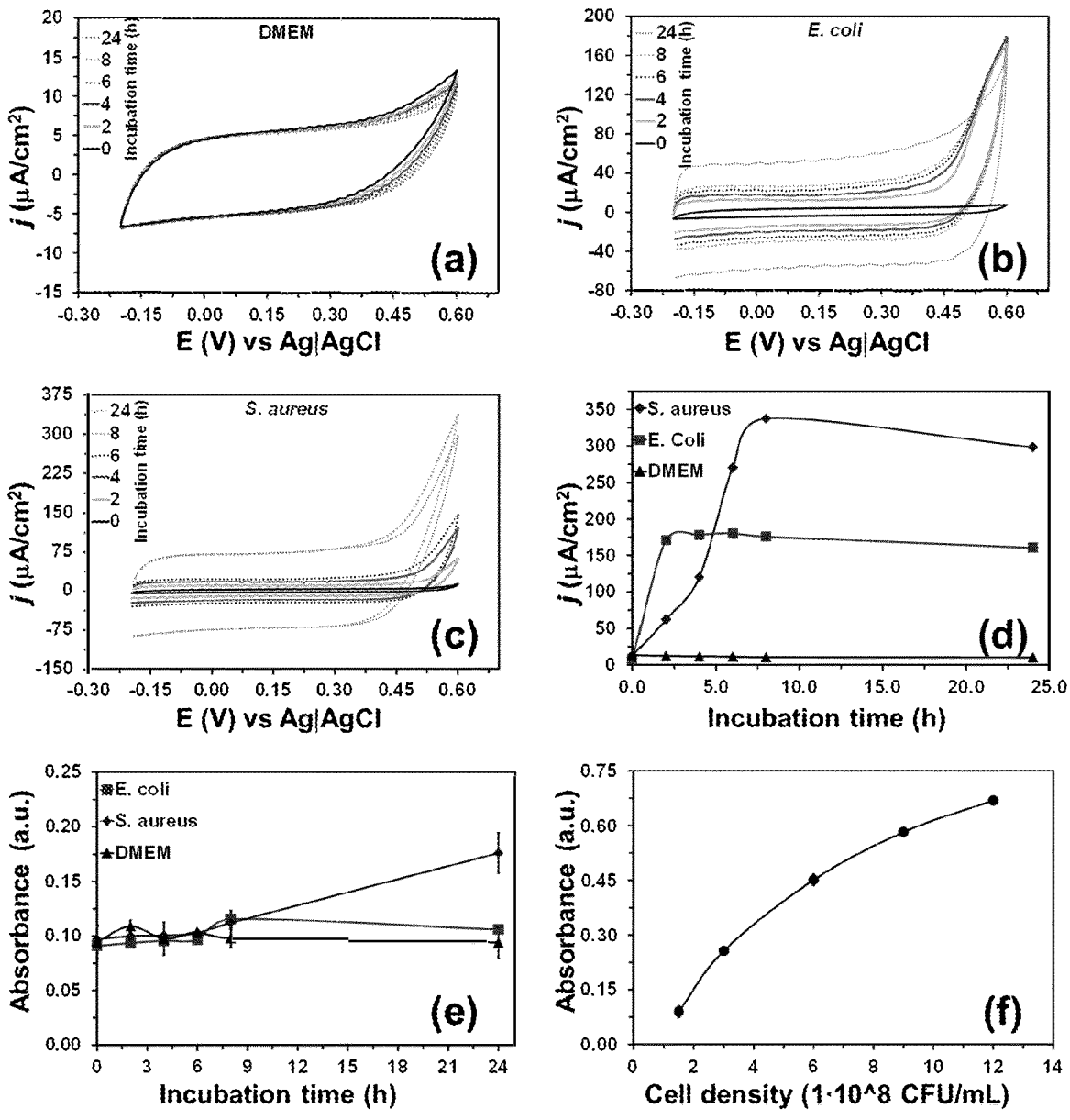

FIG. 13: Cyclic voltammograms for i-PP/PEDOT(40%) in the culture medium recorded at different incubation times: (a) in absence of bacteria; (b) in presence of *E. coli*; and (c) in presence of *S. aureus*. Initial and final electrical potentials: −0.20 V; reversal electrical potential: 0.60 V; and scan rate: 100 mV/s. (d) Variation of the current density at 0.60 V (10.6) with the incubation time for (a), (b) and (c). (e) Variation of the absorbance at 450 nm with the incubation time as determined in the culture medium in absence of bacteria and in presence of *E. coli* and *S. aureus*. (0 Calibration curve obtained using the McFarland standard to approximate the number of bacteria as a function of the absorbance.

Figure 14:
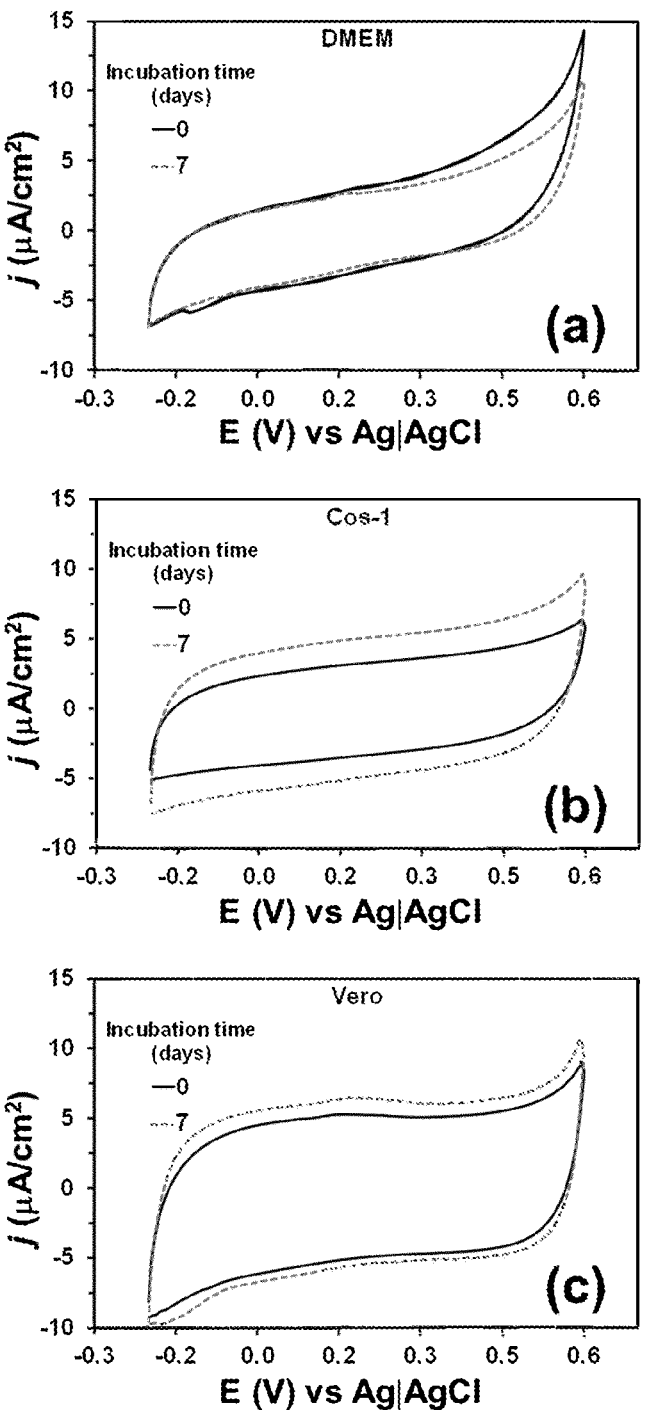

FIG. 14: Cyclic voltammograms for i-PP/PEDOT(40%) in the culture medium recorded just after the addition of the cells and after seven days of incubation: (a) in absence of cells; (b) in presence of Cos-1 cells; and (c) in presence of Vero cells.

Figure 15:
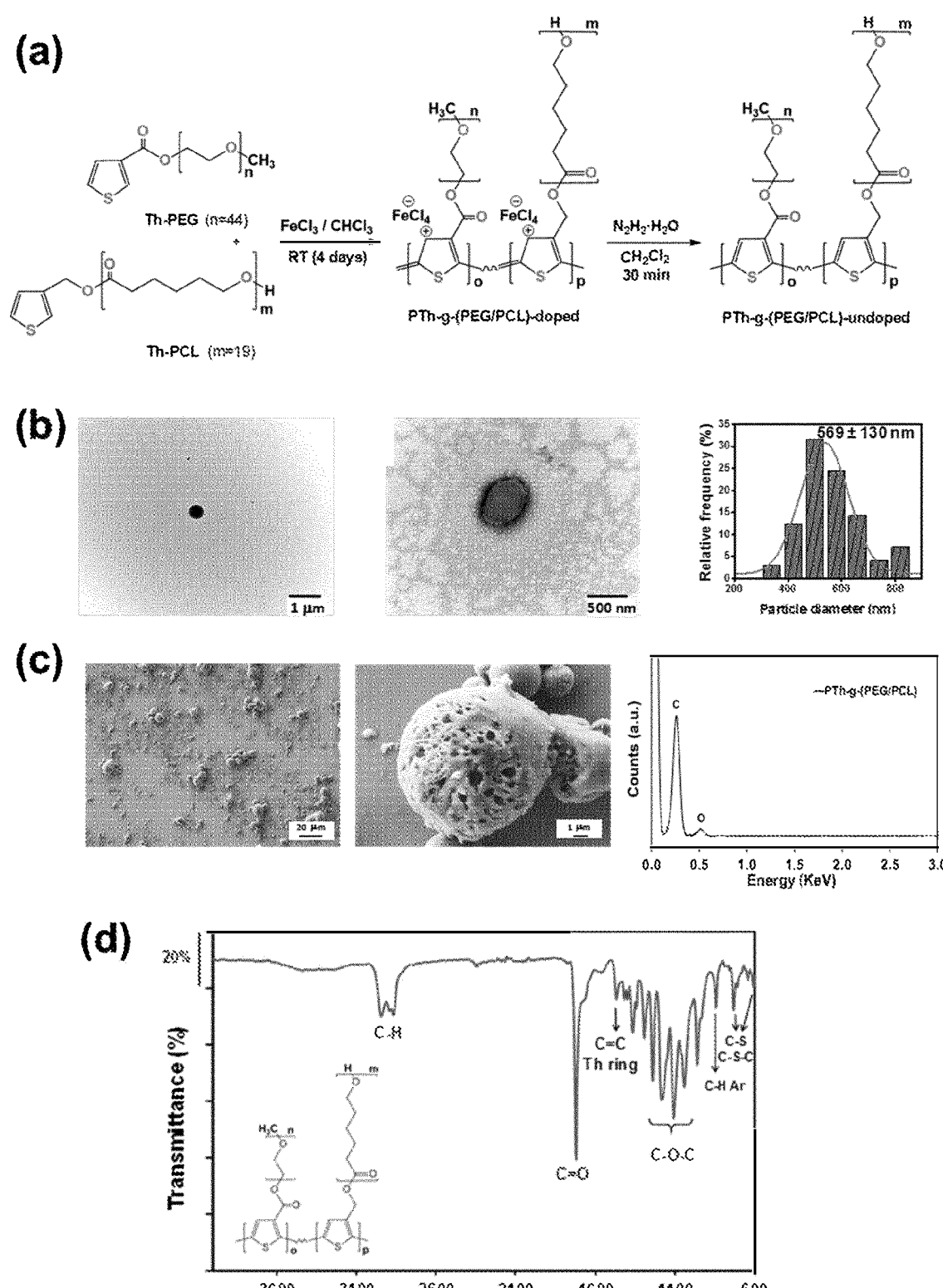

FIG. 15: (a) Synthesis of PTh-g-(PEG/PCL) copolymer. (b) TEM micrograph of PTh-g-(PEG/PCL) particles: with and without uranyl acetate staining (left and center, respectively) and size particle distribution (right). (c) SEM micrographs of PTh-g-(PEG/PCL) microparticles (left and center) and EDX spectrum from particle showed in the center micrograph. (d) Infrared spectrum of PTh-g-(PEG/PCL) copolymer.

Figure 16:
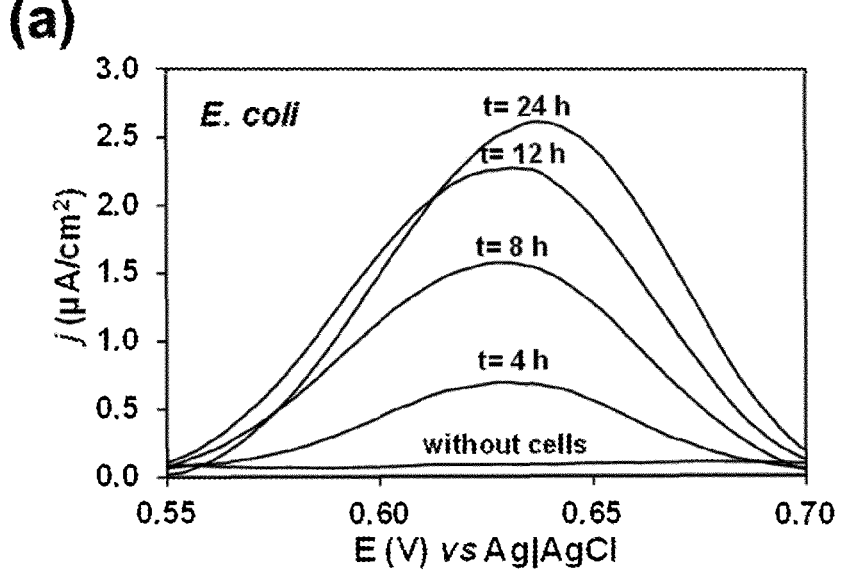
Figure 16:
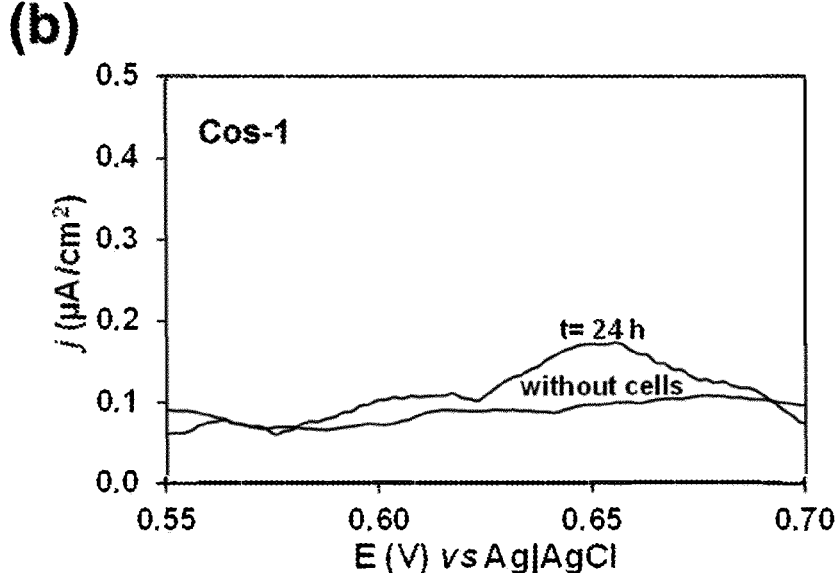

FIG. 16: DPV for PTh-g-(PEG/PCL) supported onto vitreous carbon after 6 h of incubation in culture medium without cells (label: without cells) and recorded in presence of (a) E. Coli and (b) Cos-1 cells. Different incubation times (t=4, 8, 12 and 24 h) are displayed for E. Coli, while the only incubation time displayed for Cos-1 corresponds to 24 h.

Figure 17:
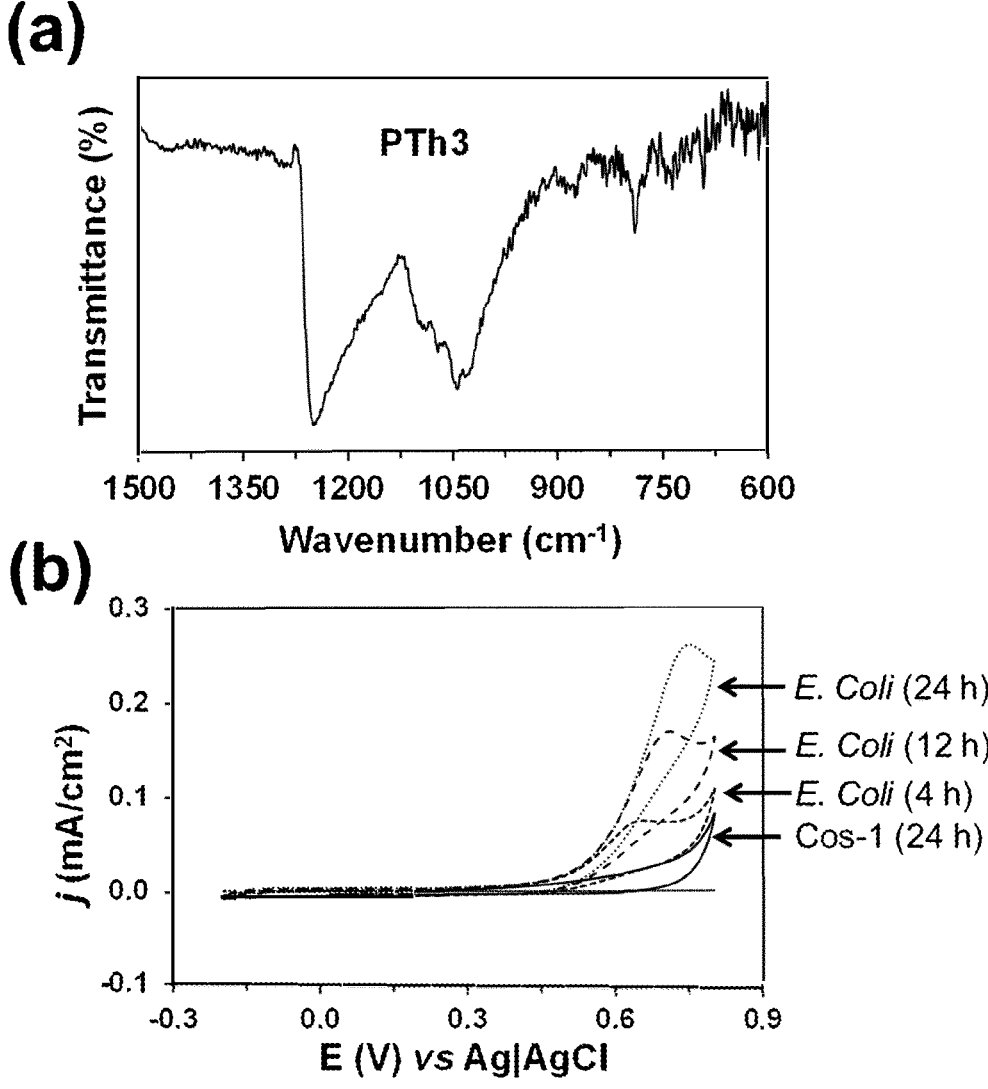

FIG. 17: (a) FTIR of PTh$_3$ and (b) cyclic voltammograms recorded for PTh$_3$ supported onto biocompatible steel after 4, 12 and 24 h of E. Coli incubation and after 24 h of Cos-1 cells incubation.

Figure 18:
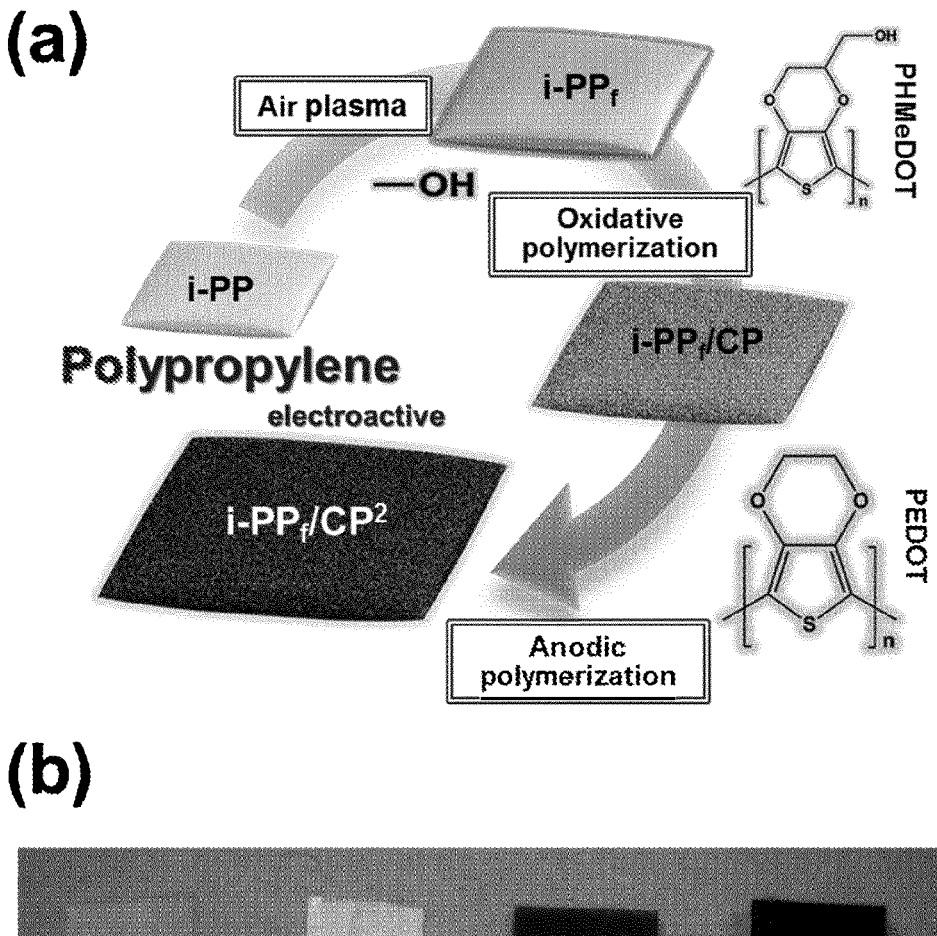

FIG. 18: (a) Sketch representing the three steps used to transform i-PP into i-PP/CP$^2$, and electroactive i-PP with sensing properties. (b) Photographs of pristine i-PP, i-PP/CP and i-PP/CP$^2$ films.

Figure 19:
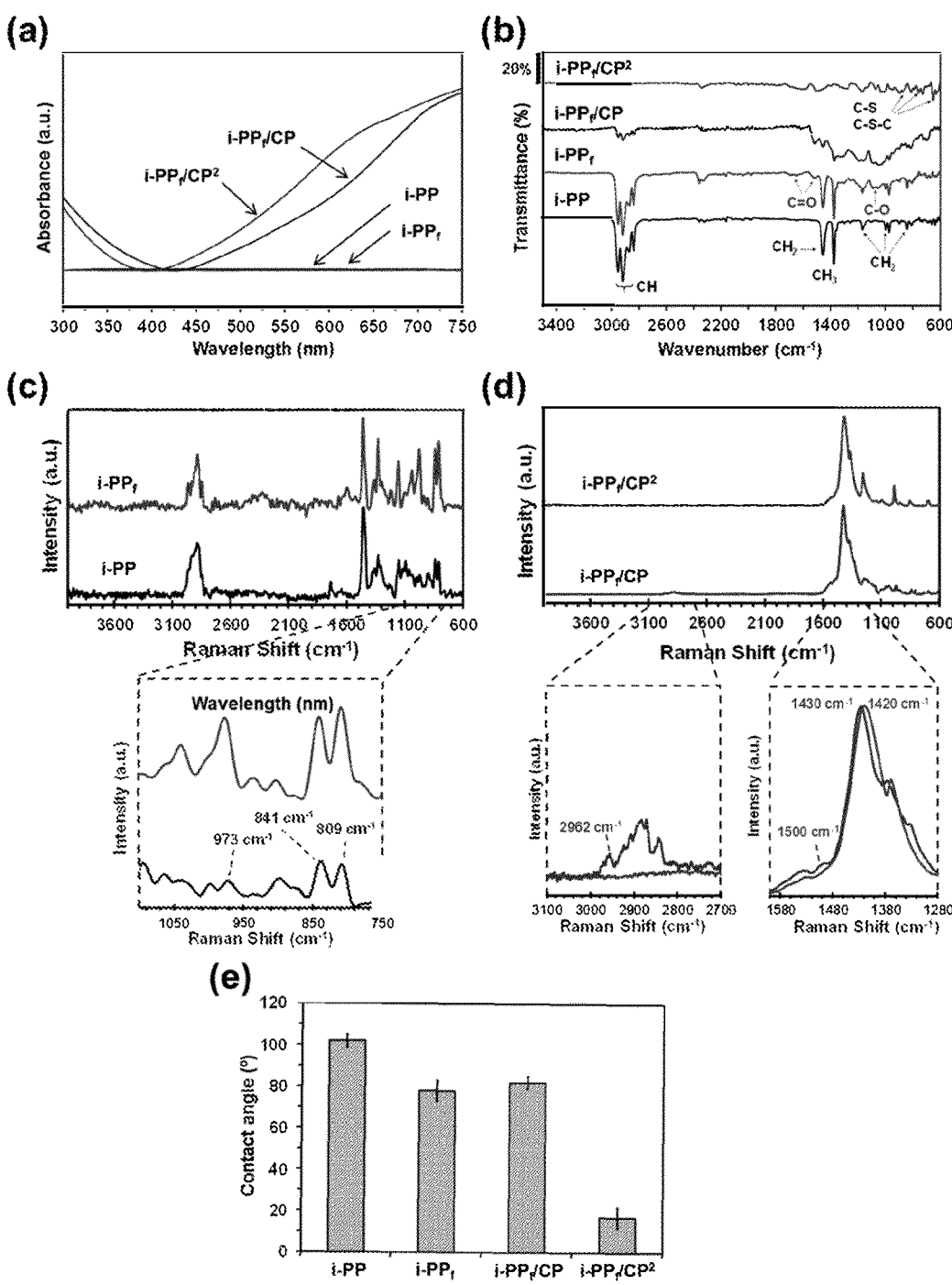

FIG. 19: (a) UV-Vis, (b) FTIR and (c, d) micro-Raman spectra i-PP, i-PP/CP and i-PP/CP$^2$. The contact angles of such four systems as obtained for water are compared in (e).

Figure 20:
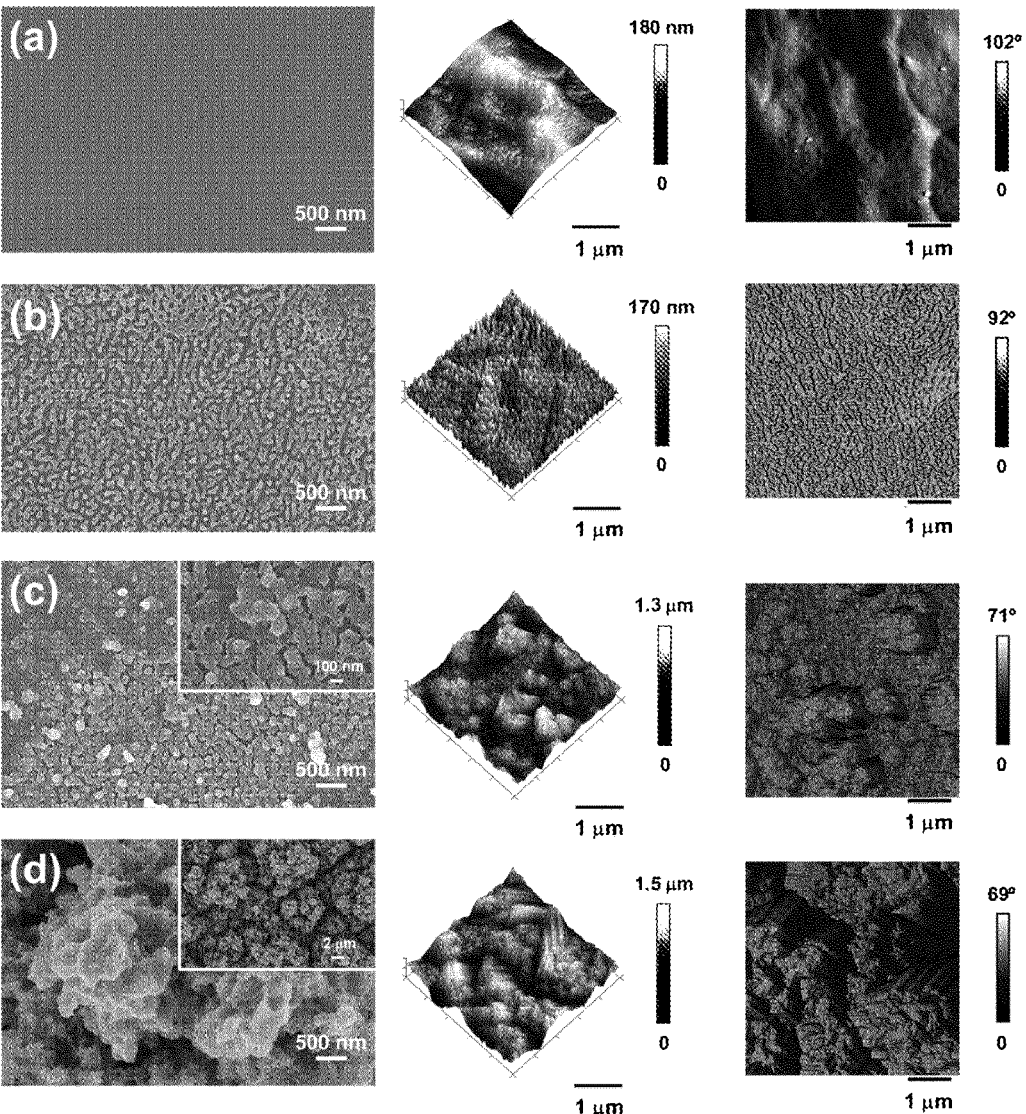

FIG. 20: High resolution SEM micrograph (left), 3D height and phase AFM images (center and right, respectively) of (a) i-PP, (b) (c) i-PP/CP and (d) i-PP/CP$^2$.

Figure 21:
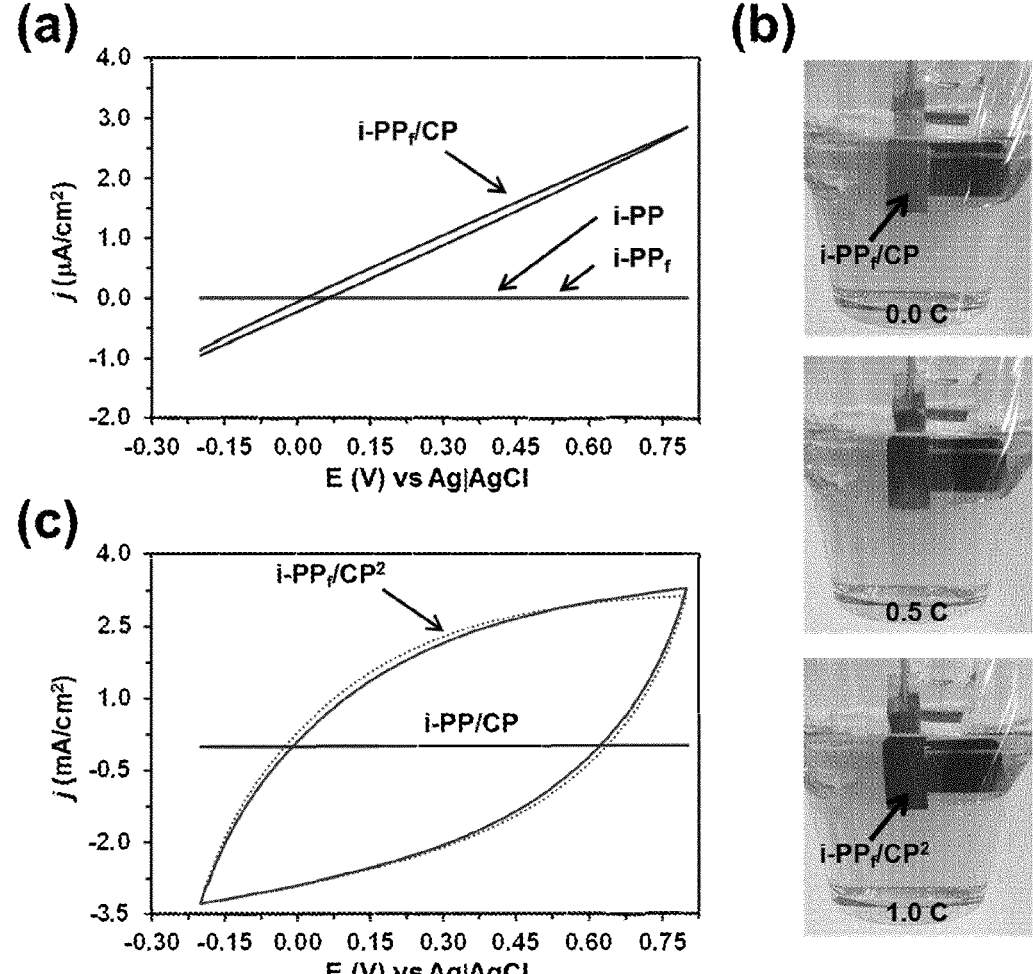

FIG. 21: (a) Control voltammograms of i-PP, i-PP$_f$ and i-PP/CP in PBS. (b) Photographs displaying the progressive variation of the colour when i-PP/CP transforms into i-PP/CP$^2$ by polymerizing the upper PEDOT layer. (c) Control voltammograms of i-PP/CP and i-PP/CP$^2$ in PBS. The voltammogram recorded for i-PP/CP$^2$ after 50 consecutive oxidation-reduction cycles is also displayed (dotted curve).

Figure 22:
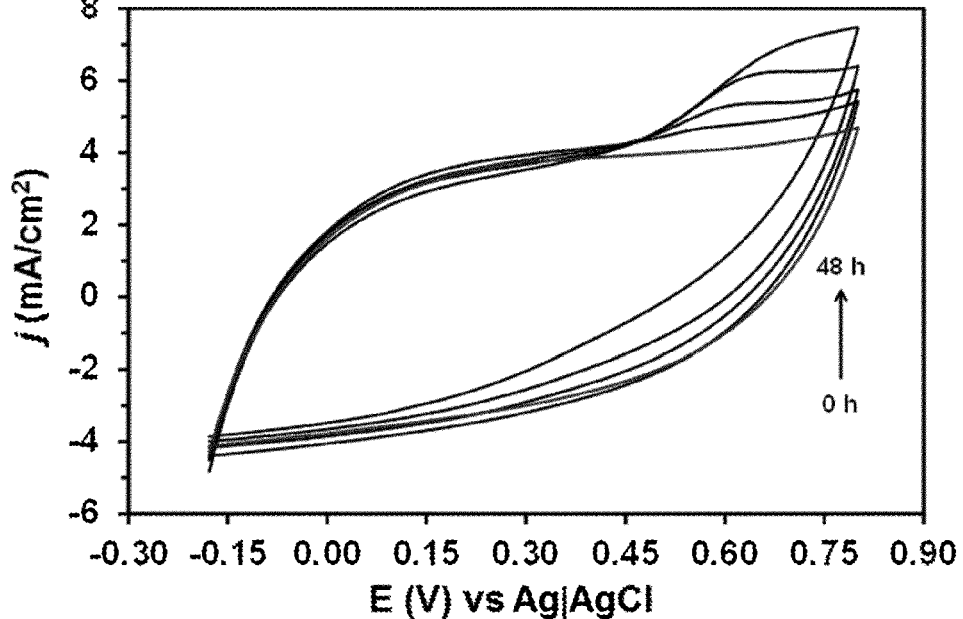

FIG. 22: Control voltammograms for i-PP/CP$^2$ in the culture medium recorded at different incubation times (from 0 to 48 h spaced by 12 h intervals). Initial and final electrical potentials: −0.20 V; reversal electrical potential: 0.60 V; and scan rate: 100 mV/s.

DETAILED DESCRIPTION

Present invention correlates the presence of NADH with bacterial infection. The invention can also correlate the presence of NADH with other microbial agents such as fungi (e.g. Candida albicans, among others) or yeasts.

Embodiments of the present invention provide a method for selective detection of bacterial and/or fungi or yeasts microbial infections through the detection of a concentration of NADH coming from a bacterial culture. The concentration of NADH is detected by means of a cyclic voltammetry or chronoamperometry applied to an electrochemically active polymer.

Embodiments of the present invention also provide an electrochemical sensor for selective detection of bacterial infections. The proposed electrochemical sensor comprises a solid substrate, e.g. a thread, a film, a suture, a mesh, a 3D structure, among others, acting as support, which is particularly made of a non-toxic and biocompatible material, not limitative as other material types could be equally used. In particular, the solid support is made of polypropylene such as isotactic polypropylene (i-PP), however other materials can be equally used for example polyesters, polyamides, polycarbonates, vitreous carbon, a hydroxyapatite, or even metals (such as platinum, gold, stainless steel, titanium, or magnesium alloys).

The proposed electrochemical sensor also includes an electrochemically active polymer, in particular poly(3,4- ethylendioxythiophene) (PEDOT) or its hydroxylated derivative, poly(hydroxymethyl-3,4-ethylenedioxythiophene (PMHeDOT), which can be in the form of particles, a thread and/or an electropolymerized film, deposited on the top of said support and configured to be electrochemically activated by a cyclic voltammetry or chronoamperometry.

The electrochemical sensor can be placed over the surface, part of the surface or inside of a medical device, such that once said cyclic voltammetry or chronoamperometry is applied, the PEDOT particles, thread or film can detect NADH through oxidation of the NADH molecules into NAD+, allowing detecting prokaryotic cells while eukaryotic cells remain undetected. In other embodiments, the electrochemical sensor can be placed over or inside other devices, for example air or water filters.

That is, present invention can detect selectively the growth of Gram-negative or Gram-positive bacteria through the oxidation of the NADH, which comes from bacterial metabolism and permeates through the outer membrane to the culture medium. In contrast, the NADH pool produced by the respiration of eukaryotic cells remains in the mitochondria and, therefore, these cells are not detected by the invention.

Following an embodiment of the preparation and characterization of the invention is detailed.

Identification of NADH from Bacteria Respiration Reactions.—

The absorption peak of NADH was identified at λ=340 nm by recording the UV-Vis spectrum in the absorbance mode (250-800 nm) of a 0.25 mM NADH solution in DMEM high glucose supplemented with 2% FBS (pH 8.1) and 0.2% NaHCO$_3$. The spectrum was acquired on a quart cell (1 mL) using a UV-Vis Cary 100 Bio (Varian) spectrophotometer. Then, a calibration curve was determined by measuring the absorbance at λ=340 nm with a Synergy HXT multi-mode reader using 0-2 mM NADH solutions in DMEM high glucose supplemented with 2% FBS (pH 8.1) and 0.2% NaHCO$_3$.

In order to prove that bacteria cellular membranes are permeable to NADH, bacteria Escherichia coli (E. coli) and Staphylococcus aureus (S. aureus) colony forming units (CFU, 2·10$^8$ colony) per mL were seeded in DMEM high glucose supplemented with 2% FBS (pH 8.1) and 0.2% NaHCO$_3$. After 24 h, 150 μL were added to 5 mL of the same supplemented medium in sterile vials. The E. coli bacteria used for this purpose were a biofilm-positive strain (B+) and a biofilm-negative strain (B−). Samples were vortexed for 1 min and incubated at 37° C. with agitation at 80 rpm for 24 h and 48 h for bacteria growth. The UV absorbance was measured at λ=340 nm in flat-bottomed 96-well plates with aliquots of culture media (200 μL) using a Synergy HXT multi-mode reader.

Synthesis of the Electrochemically Active Polymer.—

PEDOT nanoparticles were prepared as reported by Puig-gali-Jou et al. Adv. Health. Mater., 2017, 6, 1-11. In brief, an aqueous micellar solution was prepared by stirring (750 rpm) a solution of 0.07 g of DBSA in 20 mL of milli-Q water for 1 hour. This was followed by the addition of 11.8 mg of EDOT monomer and, again, was stirred (750 rpm) for 1 hour at room temperature. Finally, 0.45 g of APS dissolved in 5 mL of milli-Q water was added to the solution. Then, the reaction was maintained in agitation at 30° C. for 24 hours protected from light with aluminum foil. In this process, the color of the reaction mixture changed from light grey to dark blue.

No sedimentation was observed after the reaction, indicating a good colloidal stability. The resultant solution was centrifuged (11000 rpm) for 40 min at 4° C. The supernatant solution was decanted and the sediment was re-dispersed in milli-Q water using an ultrasonic bath for 15 min at 30° C. The centrifugation and re-dispersion process was conducted two more times to ensure the elimination of side products and unreacted chemicals, purifying the dispersion medium. Finally, the last product was kept under vacuum two days and, subsequently, was weighted and re-dispersed in the corresponding media at the desired concentration, before use.

Preparation of the Support.—

In order to dissolve polymer pellets composed by a biocompatible and non-conducting polymer, 3 g of i-PP ($M_n$=50000 g/mol, $M_n$=190000 g/mol, and polydispersity index=3.80) and 100 mL of xylene were loaded in a round bottom flask equipped with a magnetic stirrer. The solution was heated on an oil bath set at 130° C. and continuously stirred (250 rpm) until the pellets were completely dissolved. Then, the temperature was decreased to 120° C., maintained at such conditions for 20 min, and cooled to room temperature. After that, the polymer was precipitated by adding 400 mL of methanol. The polymer was separated by filtration, washed with methanol for three times, and put in a desiccator during 48 hour for solvent evaporation. The recovered product was completely dried at 50° C., in a vacuum oven, for 24 hours.

i-PP support, in this particular case in the form of films, were prepared in a hydraulic press of 15 tons equipment with Atlas series heated platens. For this purpose, 0.1 g of polymer powder were placed in the press, heated until 180° C. and, after 5 min, the pressure was increased from 0 to 5 tons. After 2.5 min, the pressure was increased to 7 tons and maintained for 2.5 min more. Finally, the film was removed from the press and cooled to room temperature.

Preparation of Porous i-PP Films.— i-PP powder was composited with 10% w/w NaCl by milling at 1000 rpm for 12 hours. Films were obtained by pressing the powder mixture following the procedure previously explained. Porous films were obtained by dissolving the NaCl particles with deionized water at room temperature. Films were kept immersed for periods of 12 hours until the weight of the dry sample was stable (i.e. water was changed every period). Hereafter, the porous films resulting from such process have been denoted i-PP(p), to differentiate them from compact i-PP films.

Preparation of i-PP/PEDOT Films.— i-PP/PEDOT films were prepared incorporating PEDOT nanoparticles to the procedure described for i-PP(p). PEDOT nanoparticles were added considering 40 or 60% w/w with respect to the i-PP weight. The films resulting from such concentrations were denoted i-PP/PEDOT(40%) and i-PP/PEDOT(60%), respectively.

Characterization.—

Dynamic light scattering (DLS) studies on PEDOT nanoparticles were performed using a zeta potential analyzer manufactured by Brookhaven Instruments Corp. under the trademark NANOBROOK OMNI. Each measurement consisted of 3 runs of 120 s duration each, which were averaged to obtain the effective diameter. Samples were analyzed at 25° C. using a scattering angle of 90°.

The thickness of i-PP, i-PP/PEDOT(40%) and i-PP/PEDOT(60%) films were measured using a thickness meter manufactured by LIST-MAGNETIK under the trademark MEGA-CHECK POCKET'. Average values and standard deviations were obtained using ten independent replicas for each film composition.

Scanning electron microscopy (SEM) was used to study the surface morphology. Micrographs were obtained using a focused ion beam scanning electron microscope manufactured by Zeiss under the trademark NEON 40™ operating at 5 kV, equipped with an energy dispersive X-ray (EDX) spectroscopy system.

FTIR spectra were recorded on a spectrophotometer manufactured by Jasco, Inc. under the trademark FT/IR 4100™. The powder and films were deposited on an attenuated total reflection accessory (Top-plate) with a diamond crystal, specifically a heated single reflection diamond ATR manufactured by Specac under the trademark GOLDEN GATE™ MKII™. Samples were evaluated using the spectra manager software and, for each sample, 32 scans were performed between 4000 and 600 $cm^{-1}$ with a resolution of 4 $cm^{-1}$.

Samples were characterized by micro-Raman spectroscopy using a commercial confocal Raman microscope manufactured by Renishaw PLC under the trademark INVIA™. The Raman setup consisted of a laser (at 785 nm with a nominal 300 mW output power) directed through a microscope, in particular a specially adapted microscope manufactured by Leica under the trademark DM2700 M™, to the sample, after which the scattered light is collected and directed to a spectrometer with a 1200 lines·$mm^{-1}$ grating. The exposure time was 1 s, the laser power was adjusted to 0.1% of its nominal output power depending on the sample, and each spectrum was collected with three accumulations.

Water contact angle (WCA) measurements were carried out with the sessile drop method at room temperature. Images of milli-Q water drops (0.5 µL) were recorded after stabilization (10 s) with an OCA instrument manufactured by Data-Physics Instruments GmbH, Filderstadt under the trademark OCA 15EC™ and analyzed using software developed and sold by Data-Physics Instruments GmbH, Filderstadt under the trademark SCA20™. For each sample, the average WCA value and the corresponding standard deviation were derived from ten independent measures at least.

Uniaxial elongation tests on rectangular samples with an area of 30 mm×3 mm and a thickness of about 0.3 mm were performed using a testing machine manufactured by Zwick under the trademark Z2.5/TM1S™. Once samples were secured in the frame, tensile testing was conducted at room temperature and samples were strained at a constant deformation rate of 10 mm/min until breakage. Mechanical parameters (i.e. Young's modulus, tensile strength and elongation at break) were obtained from the recorded stress-strain curves. The value provided in this work for each system corresponds to the average± standard deviation testing 10 independent samples.

Calorimetric data were obtained by differential scanning calorimetry (DSC). The experiments were conducted under a flow of dry nitrogen with a sample weight of approximately 5 mg sealed in an aluminum pan, calibration being performed with indium. The samples were heated from 20 to 180° C. at a rate of 10° C./min, held at 180° C. for 1 min, quenched to −50° C. and, finally, re-heated to 180° C. The degree of crystallinity ($\chi_c$) was calculated from the melting thermograms by the following equation:

$$\chi_c = \frac{\Delta H_m}{\Delta H_m^0} \times 100 \tag{1}$$

where $\Delta H_m$ is the heat of fusion of the measured sample and $\Delta H_m^0$ is the heat of fusion for 100% crystalline i-PP, which was taken equal to 209 J/g, as taught by Logakis et al. Composites Science and Technology 70 (2010) 328-335.

Thermogravimetric analyses (TGA) were conducted using a Q50 thermogravimetric analyzer of TA Instruments under a flow of dry nitrogen from 30° C. to 600° C., with a heating rate of 10° C./min and around 5 mg per sample.

Cyclic voltammetry (CV) for electrochemical characterization was performed using an instrument model PGSTAT302N manufactured by Metrohm AG under the trademark to AUTOLAB™. Experiments were conducted in a phosphate buffer solution (PBS) 0.1 M (pH=7.4) at room temperature. The initial and final potentials were −0.20 V while the reversal potential was +0.60 V. A scan rate of 100 mV s$^{-1}$ was applied in all cases. An Ag|AgCl 3 M KCl and a Pt-wire were used as reference electrode and counter electrode, respectively. The working electrode in this particular case consisted on a SPE coated with a gelatin layer that was used to adhere the i-PP and i-PP/PEDOT films. Such adhesive layer was prepared by dissolving 50 mg of gelatin from porcine skin in 1 mL of milli-Q water, which was placed in an ultrasonic bath at 40° C. for 15 minutes until a clear solution was acquired. A solution drop (10 μL) was deposited onto the SPE surface and, subsequently, a round film of i-PP or i-PP/PEDOT (4 mm in diameter) was placed onto the resulting gelatin-modified SPE. The assembled working electrode was refrigerated overnight before use. The ability to exchange charge reversibly (i.e. electroactivity) was determined through direct measurement of the anodic and cathodic areas in the control voltammograms using GPES software.

Adhesion and Proliferation of Bacteria.—

*Escherichia coli* (*E. coli*) and *Staphylococcus aureus* (*S. aureus*), which are Gram-negative and Gram-positive bacteria, respectively, were selected to evaluate the adhesion and proliferation of prokaryotic cells in contact with the i-PP and i-PP/PEDOT samples. The bacteria were previously grown aerobically to exponential phase in broth culture (5 g/L beef extract, 5 g/L NaCl, 10 g/L tryptone, pH 7.2).

$2 \times 10^8$ colony forming units (CFU) per mL were seeded in 10 mL of culture DMEM high glucose supplemented with 2% FBS (pH 8.1) and 0.2% NaHCO$_3$. After 24 hours, 150 μL were added to 5 mL of fresh DMEM in sterile vials containing i-PP, i-PP(p), i-PP/PEDOT(40%) and i-PP/PE-DOT(60%) films. Controls were simultaneously performed by culturing cells in sterile vials without material. All samples, including the control, were vortexed for 1 min and incubated at 37° C. with agitation at 80 rpm for 24 hours and 7 days for cell growth. UV absorbance was measured at λ=450 nm in a flat-bottomed 96 well-plates with aliquots of 200 μL. The results, derived from the average of three replicates (n=3) for each independent experiment, were normalized with the control for relative percentages.

Adhesion and Proliferation of Eukaryotic Cells.—

Cellular assays were performed using Cos-1 and Vero cells. These cells were selected due to their fast growth. Cells were cultured in DMEM high glucose buffered with 2.5 mM of HEPES, 10% FBS, penicillin (100 units/mL), and streptomycin (100 μg/mL). The cultures were maintained in a humidified incubator with an atmosphere of 5% CO$_2$ and 95% 02 at 37° C. Culture media were changed every two days. When the cells reached 80-90% confluence, they were detached using 2 mL of trypsin (0.25% trypsin/EDTA) for 2-5 min at 37° C. Finally, cells were re-suspended in 5 mL of fresh medium and their concentration was determined by counting with a Neubauer camera using 0.4% trypan blue as a vital dye.

i-PP and i-PP/PEDOT films were placed in plates of 24 wells and sterilized using UV irradiation for 15 min in a laminar flux cabinet. Controls were simultaneously performed by culturing cells on the surface of TCPS plates. For adhesion and proliferation assays $2 \times 10^4$ and $1 \times 10^4$ Cos-1 and Vero cells, respectively, were deposited on the film of each well. Then, attachment of cells to the film surface was promoted by incubating under culture conditions for 30 min. Finally, 2 mL of the culture medium were added to each well. After 24 h, cellular adhesion was determined by quantifying the cells attached to the films or the control. Cellular proliferation was evaluated by quantifying the viable cells onto the evaluated materials after 7 days of culture.

Cellular viability was evaluated by the colorimetric MTT [3-(4,5-dimethylthiazol-2-yl)-2,5-diphenyltetrazolium bromide] assay. This assay measures the ability of the mitochondrial dehydrogenase enzyme of viable cells to cleave the tetrazolium rings of the MTT and form formazan crystals, which are impermeable to cell membranes and, therefore, are accumulated in healthy cells. This process is detected by a color change: the characteristic pale yellow of MTT transforms into the dark-blue of formazan crystals. Specifically, 50 μL of MTT solution (5 mg/mL in PBS) were added to each well. After 3 h of incubation, samples were washed twice with PBS and stored in clean wells. In order to dissolve formazan crystals, 1 mL of DMSO/methanol/water (70/20/10% v/v) was added. Finally, the absorbance was measured in a plate reader at 570 mm. The viability results, derived from the average of three replicates (n=3) for each independent experiment, were normalized to the control, for relative percentages.

Electrochemical Detection of Prokaryotic and Eukaryotic Cells.—

The selective electrochemical detection of prokaryotic and eukaryotic cells was performed by CV using the experimental conditions described above with exception of the PBS electrolytic solution, which was replaced by the corresponding cell culture media. All experiments were replicated three times.

Results.—

As the invention is related with the identification of bacterial infection through the detection of NADH coming from microbial respiration reactions, it has been proved such relationship between the content of NADH in a physiological medium and the amount of bacteria. For this purpose, *E. coli* bacteria were seeded ($2 \cdot 10^8$ colony forming units per mL) in DMEM supplemented with FBS and NaHCO$_3$. The bacteria used for this purpose were a biofilm-positive strain (B+), and a biofilm-negative strain (B−). Then, colonies were incubated at 37° C. and 150 rpm for 24 h and 48 h maintaining conditions. After such periods of time, the concentrations of NADH in the culture media were determined by measuring the absorbance at λ=340 nm and applying the calibration curve displayed in FIG. 1. This curve was obtained by determining the UV absorption at λ=340 nm of DMEM solutions supplemented with FBS, NaHCO$_3$ and different NADH concentrations (from 0 to 2 mM). The calibration curve consists on the absorbance of the peak at λ=340 nm, which corresponds to NADH, vs. the NADH concentration.

FIG. 2 represents the absorbance at λ=340 nm obtained for B+ and B− *E. coli* cultures after 24 and 48 h (left) as well as the NADH concentrations calculated by applying the corresponding calibration curve (right). The NADH concentration, which was null after seeding the bacteria in the medium, grows with time, independently of the ability to form biofilm. Thus, after 24 h the NADH concentration is 0.25 and 0.34 mM for B+ and B−, respectively, increasing 36% and 8%, respectively, after 48 h. Furthermore, the NADH concentration is higher for B− than for B+. This expected behavior has been attributed to compactness of the biofilm structure, which comprises a self-produced matrix of extracellular polymeric substances and restricts the release of NADH to the medium. In any case, the significant amount of NADH appearing in the culture media is due to the bacteria growth, demonstrating that the integration of electrochemical sensors in implants and/or prostheses can be successfully used to identify bacterial infections by detecting the NADH from microbial metabolism.

The same procedure was applied to *S. aureus* bacteria. Results, which are represented in FIG. 3 corroborate previous observations with *E. coli*, confirming that bacteria cellular membranes are permeable to the NADH from the bacteria respiration reactions. The concentration of NADH found in the *S. aureus* culture is 0.44 and 0.51 mM after 24 h and 48 h, respectively. Overall, these results confirm that bacterial infections can be successfully identified through the detection of extracellular NADH.

The synthesis of the PEDOT nanoparticles was conducted in water at 30° C. using DBSA as stabilizer and doping agent simultaneously, and APS as oxidizing agent. FIG. 4*a* displays a micrograph of the resulting PEDOT nanoparticles, which present a coral-like morphology and exhibit an effective diameter of 48±9 and 91±1 nm as determined by SEM and DLS, respectively. The FTIR spectra of EDOT monomer and PEDOT nanoparticles doped with DBSA are compared in FIG. 4*b*. The monomer shows bands at 3109 and 772 cm$^{-1}$ which correspond to the C$^\alpha$—H stretching and out-of-plane vibration modes, respectively. The disappearance of these two absorption bands in the polymer spectrum proves the success of the polymerization process, reflecting that the hydrogen atoms at the Ca-position were removed during the formation of PEDOT nanoparticles. Some characteristic bands from PEDOT correspond to the stretching modes of C═C in the thiophene ring at 1557 cm$^{-1}$, the C—O—C vibrations at 1223 and 1053 cm$^{-1}$, the stretch of the C—S bond in the thiophene ring at 834 and 681 cm$^{-1}$. The absorption band at 1646 cm$^{-1}$ is assigned to the C═C stretching vibration band of phenyl side group from DBSA. The presence of the peak at 1719 cm$^{-1}$ has been attributed to the carbonyl group formed by the irreversible overoxidation of the thiophene ring in the conducting polymer (CP), which is induced by the APS. Overoxidized PEDOT exhibits unique sensitivity and selectivity for the determination of biomolecules, such as dopamine and uric acid, successfully achieving the detection of submicromolar concentrations.

On the other hand, the average thickness of i-PP, i-PP(p), i-PP/PEDOT(40%) and i-PP/PEDOT(60%) films was 47±5, 74±5, 81±4, and 76±4 µm, respectively. Comparison of the FTIR spectra of the i-PP-based films (FIG. 4*c*) indicates that the polyolefin absorption bands completely dominate the spectra recorded for i-PP(p), i-PP/PEDOT(40%) and i-PP/PEDOT(60%) composites. Thus, all spectra show the i-PP characteristic absorption peaks in 2953, 2879, 1377, 1156 and 968 cm$^{-1}$ (stretching, deformation and rocking vibration of —CH$_3$), 2915 and 2840 cm$^{-1}$ (stretching vibration of —CH$_2$), and 1449 cm$^{-1}$ (bending vibration of —CH$_2$).

The Raman spectrum of i-PP is displayed in FIG. 4*d*. The bands associated to the fundamental frequencies of the chemical unit or due to localized vibrations within short chain segments (group frequencies) are: 809 (CH$_2$ rocking and C—C stretching), 843 (CH$_2$ rocking) 973 (CH$_3$ rocking and C—C stretching), 998 (CH$_3$ rocking), 1151 (C—C stretching, C—H bending), 1120 (CH$_2$ twisting, CH wagging and C—C stretching), and 1436 cm$^{-1}$ (CH$_2$ group deformation). Moreover, the CH$_3$ vibrations at 973 cm$^{-1}$ are attributed to the symmetry of the 3$_1$ helical conformation of crystalline i-PP chains, while the CH$_3$ rocking at 998 cm$^{-1}$ involves segments with such helical structure. The integral intensity of the bands at 809 and 843 cm$^{-1}$ was proposed to be an estimation of the degree of crystallinity (xc) of i-PP. Thus, chains in regular helical conformations present in crystals are related with the former band, while helical chains with conformational defects and chains with non-helical conformations are related with the latter one. The crystallinity value derived from the 809 and 843 cm$^{-1}$ bands was $\chi_c$=51% and 40%, respectively, the average value (46%) being fully consistent with that derived from melting thermograms (see below).

FIG. 4*d* includes the Raman spectra of PEDOT nanoparticles, i-PP/PEDOT(40%) and i-PP/PEDOT(60%). The Raman fingerprints of PEDOT were reported in previous studies. The main vibrational mode of this CP at 1424 cm$^{-1}$ and the surrounding less intense bands at 1490 and 1368 cm$^{-1}$ correspond to the symmetric C$_\alpha$═C$_\beta$ stretching, asymmetric C$_\alpha$═C$_\beta$ stretching and C$_\alpha$–C$_{\alpha'}$ inter-ring stretching vibrations, respectively. Other important bands appear at 708, 856 and 991 cm$^{-1}$ which have attributed to the symmetric C—S—C deformation, asymmetric C—S—C deformation and O—C—C—O ring deformation, respectively. In opposition to FTIR observations, the Raman spectra of i-PP/PEDOT films, in which practically all the bands detected for PEDOT nanoparticles are clearly identified, look very different from the spectrum of the neat i-PP. Thus, the complementary information provided by the FTIR and Raman spectra of i-PP/PEDOT films confirms the integration of PEDOT nanoparticles into the polyolefin matrix.

FIG. 5 displays photographs and SEM micrographs of the different films prepared in this work. The whitish color of neat i-PP films turns into very dark blue when the PEDOT nanoparticles are incorporated. On the other hand, i-PP exhibits an homogeneous and compact surface morphology, whereas a distribution of closed and non-interconnected micropores, caused by the dissolution of NaCl crystals, are clearly distinguished on the surface of i-PP(p) films. Thus, the concentration of NaCl, which are incompatible with the polymer matrix, is too low to create contact between particles, precluding the formation of networks of interconnected pores crossing the entire film thickness. i-PP/PEDOT micrographs present light spots distributed on the surface, which correspond to micro-aggregates of PEDOT nanoparticles, as was proved by the signal of sulfur in the EDX analyses (FIG. 6). As it was expected, both the size and amount of spots, which are responsible for the change of color of i-PP film, increase with the concentration of PEDOT nanoparticles. More specifically, the average diameter of the micro-aggregates is 4.0±1.1 and 5.1±2.4 µm for i-PP/PEDOT(40%) and i-PP/PEDOT(60%), respectively.

Wettability, which is related with the surface topography, affects the cellular response of materials. The WCA of PEDOT films was reported to be ~80°, reflecting a hydrophilic behavior that was essentially attributed to the oxygen atoms of the fused dioxane rings. However, the WCA values measured for the different films prepared in this work, which are compared in FIG. 7*a*, indicates that PEDOT nanoparticles do not cause significant changes in the hydrophobic response of i-PP (i.e. WCA>90° in all cases). The alteration of the surface topography by adding NaCl to induce the formation of non-interconnected pores or by introducing PEDOT nanoparticles only reduced the WCA of neat i-PP (108°±1°) by 9-13°.

On the other hand, the incorporation of pores and, especially, PEDOT nanoparticles was in detriment of the mechanical properties of i-PP (FIGS. 7b-d). The addition of PEDOT nanoparticles drastically reduced the Young modulus (~50%), the tensile strength (~70%) and the elongation at break (~50%), which has been attributed to the aggregation of PEDOT nanoparticles. Thus, the CP aggregates act as fracture sites participating in the initiation and/or propagation of the mechanical failure. Obviously, these effects are more pronounced with increasing nanoparticles concentration since the interfacial adhesion between the i-PP matrix and the PEDOT aggregates become weaker, facilitating the detachment of the latter from the matrix. Also, the incorporation of PEDOT nanoparticles drastically reduces the ductility of i-PP matrix, which undergoes a stiffening effect that results in a drastic decrease of the elongation at break.

DSC melting and crystallization curves of neat i-PP and i-PP/PEDOT composites are shown in FIGS. 8a and 8b, respectively, while the characteristics from those runs are summarized in the following table.

TABLE 1

Characteristic thermal parameters for neat i-PP and i-PP/
PEDOT composites: Melting temperatures ($T_{m1}$ and $T_{m2}$), heat
of fusion ($\Delta Hm$), crystallization temperature ($T_c$), heat
of crystallization ($\Delta Hc$) and degree of crystallinity ($\chi_c$).

| Sample | $T_{m1}/T_{m2}$ (° C.) | $\Delta H_m$ (J/g) | $T_c$ (° C.) | $\Delta H_c$ (J/g) | $\chi_c$ (%)$^a$ |
|---|---|---|---|---|---|
| i-PP | 155/162 | 81 | 122 | 91 | 44 |
| i-PP/PEDOT(40%) | 158/164 | 70 | 125 | 76 | 36 |
| i-PP/PEDOT(60%) | 160/163 | 70 | 127 | 68 | 33 |

$^a$Heat of fusion for 100% of crystalline i-PP: 209 J/g

Neat i-PP displays two melting peak temperatures ($T_{m1}$ and $T_{m2}$) at $T_{m1}$=155° C. and $T_{m2}$=162° C., which correspond to the melting of the β- and α-form crystals, respectively. Incorporation of PEDOT nanoparticles results in small shifts of the $T_m$ values (e.g. $T_{m1}$=158° C. and $T_{m2}$=164° C. for i-PP/PEDOT(40%)), which have been attributed to small increments of the crystal sizes, and in an enhancement of the heat flow at the $T_{m2}$ peak, which illustrates that PEDOT nanoparticles favors the formation of α-type i-PP. Besides, when cooled at 10° C./min, the crystallization temperature ($T_c$) of neat i-PP ($T_c$=122° C.) increases 3-4° C. upon the incorporation of PEDOT nanoparticles, suggesting that the latter act as nucleating agents. However, the degree of crystallinity ($\chi_c$), which was calculated from the melting thermograms (Eqn 1), decreases upon the incorporation of CP nanoparticles, evidencing that size of the crystals grown around such nucleating agents ($\chi_c$=33-36% for i-PP/PEDOT) is smaller than that of crystals in neat i-PP ($\chi_c$=44%). This could be attributed to the poor interfacial adhesion between i-PP crystals and PEDOT nanoparticles.

The influence of PEDOT nanoparticles on the thermal stability of i-PP was investigated by TGA at a heating rate of 10° C./min. FIG. 8c shows that the CP Nanoparticles affect the thermal stability of the i-PP matrix. More specifically, although the decomposition starts at a lower temperature for the composites than for the neat polymer, the temperature of 70% of weight loss ($T_{0.7}$) is lower for i-PP homopolymer ($T_{0.7}$=450° C.) than for the i-PP/PEDOT ($T_{0.7}$=462 and 459° C. for 40% and 60% composites, respectively). Furthermore, the derivative of the TGA curves (DTGA) reveals that i-PP follows a one-step decomposition pattern with a maximum at $T_{max}$=448° C., whereas the two i-PP/PEDOT composites present a more complex mechanism that depends on the concentration of CP nanoparticles. Thus, the DGTA curve obtained for i-PP/PEDOT(40%) displays a maximum at $T_{max,1}$=457° C. and a shoulder at $T_{max,2}$=370° C., while i-PP/PEDOT(60%) shows a peak centered at $T_{max,1}$=446° C. and two shoulders at $T_{max,2}$=424° C. and $T_{max,3}$=355° C. Such shoulders have been related to concentration-dependent degradation steps of PEDOT nanoparticles.

Control voltammograms for bare and film-modified SPEs in 0.1 M PBS (pH 7.4), are displayed in FIG. 9a. Although the voltammograms recorded for i-PP(p)-modified SPEs exhibit electroactivity, the lack of anodic and cathodic peaks indicates that oxidation and reduction processes do not occur at specific positions of i-PP polymer chains. Amazingly, the area of the voltammograms recorded for i-PP(p)-modified electrodes increases with the number of oxidation-reduction cycles, as proves the comparison of the anodic and cathodic areas obtained for the control voltammogram with those of voltammograms recorded after 10, 20, 50, 100, 250 and 500 redox cycles (FIG. 9b). Specifically, the voltammetric charge grows from 7±3 µC (first control voltammogram) to 19±2 µC after 500 redox cycles (FIG. 9e), stabilizing at such value, which represents an increment of ~270% in terms of electroactivity (FIG. 90. Moreover, after approximately 20 redox cycles, the shape of the voltammogram changes, becoming similar to that of bare SPE. Both the increment of electroactivity and variation in the shape suggest that i-PP/NaCl(p) films undergo degradation during the electrochemically induced redox processes (see below).

On the other hand, the control voltammograms of the two i-PP/PEDOT composites (FIG. 9a) resemble those reported for neat PEDOT films, with an anodic peak at approximately −0.1 V and a cathodic peak at a potential slightly lower than the reversal potential. It should be noted that the mechanical resistance of anodically polymerized PEDOT is null, the obtaining of self-supported films being completely impossible. Although the current density increases with the concentration of PEDOT nanoparticles, it is significantly lower than that reported for nanometric PEDOT films, indicating that CP aggregates remain isolated inside the i-PP matrix, as was observed in SEM micrographs (FIG. 5). Additionally, the anodic and cathodic areas of the voltammograms recorded for i-PP/PEDOT(40%) and i-PP/PEDOT(60%) also increase with the number of consecutive redox cycles (FIGS. 9b and 9c, respectively) in a similar manner than i-PP(p). However, this infrequent "self-electrostabilizing" effect is much more pronounced for latter composite than for the former one. Thus, the voltammetric charge of i-PP/PEDOT(40%) and i-PP/PEDOT(60%) increases from 17±3 to 32±2 µC and from and 13±3 to 56±4 µC (FIG. 9e), respectively, after 500 consecutive redox cycles, Those variations represent an increment in the electroactivity of ~190% and ~330% (FIG. 90, respectively.

The increment of the oxidation and reduction areas of the voltammograms has been previously observed in some complex CPs, as for example in graft copolymers with a polythiophene backbone and chains of poly(ethylene glycol) with well-defined molecular weight ($M_w$=2000) grafted to the backbone (PTh-g-PEG$_{2000}$) doped with perchlorate anions. In that case, the porosity of the material increased with the number of cycles, facilitating the access and escape of the dopant ions during the oxidation and reduction processes, respectively. Accordingly, PTh-g-PEG$_{2000}$ became a self-electrostabilized material because of the electrochemically-induced structural changes at the $PEG_{200}$ side chains.

The FTIR spectra recorded before and after 500 consecutive redox cycles are very similar for i-PP(p) and i-PP/PEDOT (FIG. 10), indicating that i-PP does not undergo significant chemical changes. Therefore, the self-electrostabilizing effect observed in FIGS. 9b-d cannot be attributed to the chemical degradation of the i-PP matrix. In contrast, SEM images of i-PP(p) and i-PP/PEDOT after 500 redox cycles, which are displayed in FIG. 11, indicate important structural changes in the surface of the sensor system. As it can be seen, the porosity of the i-PP(p) films increases after 500 cycles due to the appearance of microfractures on the surface (FIG. 11a), which are caused by the stress induced by consecutive scans of potential. In the case of i-PP/PEDOT(40%) and i-PP/PEDOT(60%) (FIGS. 11b and 11c, respectively), the structural stress induced by potential scans is adsorbed by some PEDOT aggregates that end up detaching. Obviously, the shape and size of the resulting pores are defined by the characteristics of detached PEDOT particles, which are very varied. The increment of the surface porosity facilitates the access and escape of the ions during the oxidation and reduction processes, respectively, and explains the unusually observed self-electrostabilizing behavior.

The adhesion and proliferation of prokaryotic and eukaryotic cells onto i-PP, i-PP(p), i-PP/PEDOT(40%) and i-PP/PEDOT(60%) samples were evaluated considering different bacteria and cell lines. Regarding to prokaryotic cells, *E. coli* and *S. aureus*, which are Gram-negative and Gram-positive bacteria, respectively, were incubated onto such films. The extent of the antimicrobial activity was quantified by analyzing the turbidity of the incubated bacteria cultures after 24 hours and 7 days, which was related to the bacterial growth, by UV-vis spectroscopy at $\lambda$=450 nm. Inspection of the relative viabilities after 24 hours (FIG. 12a, left), which are very similar to that displayed by the TCPS control, shows that bacteria do not exhibit a specific attraction towards i-PP, i-PP(p) and i-PP/PEDOT films. However, bacterial growth was observed after 7 days, especially onto i-PP/PEDOT films (FIG. 12a, right), relative to the control. More specifically, i-PP and i-PP(p) apparently inhibits the proliferation of *E. coli* and promotes the growing of Gram-positive bacteria, whereas PEDOT-containing samples benefits the growth of both Gram-positive and Gram-negative bacteria. Obviously, this effect could be mitigated by loading bactericidal agents into the i-PP film and/or the CP nanoparticles, as for example gramicidin and $A_g^+$, which retain their antimicrobial activity when combined with synthetic polymers.

The abilities of i-PP, i-PP(p), i-PP/PEDOT(40%) and i-PP/PEDOT(60%) films to enhance the adhesion and proliferation of eukaryotic cells are compared in FIG. 12b (right and left, respectively). As it can be seen, the cellular adhesion onto the composite films is conditioned by the i-PP matrix, which presents the lowest relative viability for Vero and, especially, Cos-1 cells. Specifically, after 24 h, Cos-1 viability is ~40% lower for i-PP and i-PP/(p) than for the control, while the incorporation of CP results in an increment of the viability that depends on the Nanoparticles concentration. Cell adhesion affects cell proliferation (FIG. 12b, right), the number of cells on the surface of the films after 7 days being higher than after 24 hours for all films. Results confirm that cell adhesion is easier onto the composite films than onto the i-PP ones, this tendency increasing with the concentration of PEDOT nanoparticles. Thus, although the viabilities obtained for the Vero cell line are higher for all prepared films than for the control, Cos-1 cells clearly prefer the composite films than the i-PP and i-PP(p) films. This behavior has been attributed to the ion exchange ability of the electroactive CP, which favors the exchange of electrolytes with cell at the interface defined by the surface of the film and the cell membrane.

Now, the performance of the i-PP/PEDOT composite for the in situ electrochemical detection of biofilms contamination is examined. With the aim of orienting the electrochemical sensor towards clinical applications, the fingerprints of eukaryotic and prokaryotic cells must be successfully differentiated. More specifically, in a particular embodiment, the invention focused on monitoring the metabolism of bacteria and eukaryotic cells through the oxidation of NADH to NAD(+) by using carbon SPEs coated with i-PP/PEDOT(40%) films, since the load of PEDOT Nanoparticles is smaller and present properties similar to i-PP/PEDOT(60%). The growth of both bacteria and eukaryotic cells was monitored by examining the electrochemical response of the medium at different times, which range from 0 (just when the cells are introduced in the culture medium) to 24 hours.

FIG. 13a displays the response of the electrochemical sensor to the culture medium without cells at different incubation times. As it can be seen, cyclic voltammograms are similar to those displayed in FIG. 9, independently of the incubation time, indicating that the response coming from the oxidization of species contained in the DMEM solution is practically null. Accordingly, the anodic current at the reversal potential (10.6), 0.60 V, only decreases from 13 to 11 $\mu A/cm^2$ after 24 hours. In opposition, i-PP/PEDOT(40%) is remarkably affected by the presence of cultured bacteria, even though the responses of the electrochemical sensor against *E. coli* and *S. aureus* are different and change with the incubation time (FIGS. 13b and 13c, respectively). Thus, an oxidation peak at 0.60 V is clearly observed in both cases. This has been attributed to the oxidation of NADH to NAD(+) and is indicative of the bacteria activity. Moreover, the current density at 0.60 V varies with the incubation time (FIG. 13d), reflecting that i-PP/PEDOT(40%) detects that the bacteria growth is very rapid at the first stages of the incubation. For *E. coli*, $j_{0.6}$ increases from 8 to 171 $\mu A/cm^2$ after 2 hours, decreasing to 161 $\mu A/cm^2$ after 24 hours (FIG. 13d). For *S. aureus*, the $j_{0.6}$ value is 298 $\mu A/cm^2$ after 24 hours of culture (FIG. 13d), which is consistent with the cell viability measurements displayed in FIG. 12a (i.e. adhesion was higher for the Gram-positive bacterium than for the Gram-negative one). However, analysis of the temporal evolution of $j_{0.6}$ displayed in FIG. 13d allows monitoring that in the first stages the growing of *E. coli* is faster than that of *S. aureus*.

FIG. 13e displays the growth of *E. coli* and *S. aureus* against the incubation time as determined UV-vis spectroscopy. As it can be seen, the variation of the absorbance at 450 nm with the incubation time match the profiles obtained using the i-PP/PEDOT(40%) for the two bacteria (FIG. 13d), evidencing the great capacity of the electrochemical sensor for detecting the presence of growing bacteria and finally the biofilm. However, the selectivity with respect eukaryotic cells is crucial for the performance and practical application of the electrochemical sensor in medical prostheses. The calibration curve (FIG. 130, which was approximated using the McFarland standard, indicates that the amount of *E. coli* and *S. aureus* bacteria grow from $1.6 \times 10^8$ CFU/mL (first measure for both types) to $1.7 \times 10^8$ and $2.4 \times 10^8$ CFU/mL, respectively, after 24 h. These results are fully consistent with the electrochemical sensing measures displayed in FIG. 13c.

FIG. 14 proves that the electrochemical response of i-PP/PEDOT(40%) against the growth of eukaryotic cells is completely different to that displayed for bacteria. Cyclic voltammograms recorded just after the addition of Cos-1 and Vero cells are practically identical to those obtained after 24 hours of cell culture (not shown) and very similar to those achieved after 7 days of cell proliferation (FIG. 14). Moreover, after such long time $j_{0.6}$ only increases from 7 to 10 $\mu A/cm^2$ and from 9 to 11 $\mu A/cm^2$ for Cos-1 and Vero cells, respectively, evidencing that the concentration of NADH induced by such eukaryotic cells is not high enough to be detected by the i-PP/PEDOT electrochemical sensor.

Results displayed in FIGS. 13 and 14 clearly indicate that the i-PP/PEDOT(40%) electrochemical sensor is selective, allowing to distinguish bacteria from eukaryotic cells. This selectivity originates from the sensitivity of the i-PP/PEDOT composite towards the oxidation of NADH, which is high enough to detect the metabolism of bacteria but too low for the respiration of eukaryotic cells. In addition, the oxidation of NADH towards $NAD^+$ probably causes an electrochemically-induced concentration gradient, favoring the exit of cytosolic NADH to the medium through the outer bacterial membrane and, consequently, facilitating the detection of the microbial metabolism.

Following other embodiments of the application of the invention are presented.

1) Amphiphic Heterografted Polythiophene Copolymer Nanoparticles Supported onto a Biocompatible Vitreous Carbon Substrate Amphiphilic copolymers consisting of a polythiophene backbone with grafted biocompatible polycaprolactone (PCL) and polyethylene glycol (PEG) blocks, PTh-g-(PEG/PCL), have been synthetized by chemical polycondensation of the corresponding PCL- and PEG-based thiophene macromonomers (FIG. 15a). Transmission electron micrographs (TEM) show that PTh-g-(PEG/PCL) forms particles with a round-like morphology (FIG. 15b). After treatment with uranyl acetate, which is usually employed to observe non-conducting materials by TEM, unique solid spherical microparticles are observed (FIG. 15b left). This proves that the core of those particles corresponds to the conjugated PTh backbone. In contrast, a clear thin layer different from the core, which has been attributed to the PEG or PCL chains, is observed in TEM micrographs of samples with uranyl staining (FIG. 15b center). Regarding the particle diameter (FIG. 15b right), a heterogeneous distribution with values ranging from 300 to 900 nm is observed, the average value being $569 \pm 130$ nm.

FIG. 15c shows representative SEM micrographs and the EDX analysis of PTh-g-(PEG/PCL) particles obtained after solvent evaporation. When the polymer solidifies, it does not form a film but rather powder particles. As it can be seen, such particles adopt an irregular spherical-like shape with high variability in diameter and porosity. The irregular shape is probably due to the fast evaporation of the solvent, which also promote the variability in the sizes and the formation of cavities, in a similar approach to that achieved with NaCl crystals dissolution in the previous embodiment. The polarity of the long PEG and PCL units also plays an important role. They should accommodate and turn around the thiophene units, avoiding the well-known $\pi$-$\pi$ stacking typically observed in PTh and its derivatives. This change in the interaction pattern, which is caused by the amphiphilic nature of the PTh-g-(PEG/PCL) copolymer, is expected to decrease the entropy with respect to typical $\pi$-$\pi$ stacked disposition of the polythiophene chains. Moreover, the EDX spectrum displayed in FIG. 15c shows C and O atoms only, evidencing that the outer layer is constituted by the PEG/PCL branches. The sulfur atoms coming from the polythiophene backbone were hardly observed by EDX, confirming that the thiophene units are enclosed inside the spheres, as was observed above by TEM.

The FTIR spectrum of PTh-g-(PEG/PCL) (FIG. 15d) show absorption bands at 2850-2941 $cm^{-1}$, which correspond to the C—H stretching vibrations from methylene groups in the Th functionalized branches. The signature peak of the C=C bonds from the Th rings appears at 1467 $cm^{-1}$ (ring deformation), while C—S and C—S—C bonds appear at 727 and 638 $cm^{-1}$. The strong and sharp absorption band observed at 1720 $cm^{-1}$ corresponds to the stretching of the C=O bond from ester linkages, which are present in both in PCL and PEG units. The bands observed at 1362, 1291 and 1094 $cm^{-1}$ have been attributed to the C—O—C stretching from ether linkages (—O—$CH_3$ and —O—C=O) and the C—O—H from hydroxyl terminal group at PCL units. Finally, the sharp and less intense bands at 951 and 840 $cm^{-1}$ usually correspond to the out-of-plane deformations of aliphatic and aromatic C—H linkages, respectively. The PTh-g-(PEG/PCL) supported onto vitreous carbon sensor was incubated into the culture medium previously used for i-PP/PEDOT during 6 h without cells. FIG. 16a displays the DPV response of this sensor was null in this case (curve labeled as: without cells). Then, *E. coli* bacteria were cultured and the response of the invention was recorded as a function of the bacteria incubation time (i.e. t=4, 8, 12 and 24 h). FIG. 16a evidences that the copolymer catalyzes the oxidation of NADH with good current density response in a low potential range. Even when the anodic peak current decreases with the concentration of NADH, the peak potential remains almost constant between 0.62-0.65 V, for all times. The same experiment was repeated but incubating Cos-1 cells. As it can be seen in FIG. 16b, the current density response was null after 24 h of incubation. As occurred above for i-PP/PEDOT, the PTh-g-(PEG/PCL) supported onto vitreous carbon sensor detects the growth of bacteria through the oxidation of the NADH to NAD+, which comes from bacterial metabolism and permeates through the outer membrane to the culture medium. On the other hand, the NADH pool produced by the respiration of eukaryotic cells remains in the mitochondria and, therefore, these cells are not detected by the invention.

This particular response also corroborates to evidences of actuation of such polythiophene system for selective detection of bacterial infections.

2) Polyterthiophene ($PTh_3$) Films Supported onto Biocompatible Steel.

$PTh_3$ films were prepared by chronoamperometry (CA) using an instrument model PGSTAT302N manufactured by Metrohm AG under the trademark AUTOLAB™ equipped with an ECD module. Polymerization was carried out in a standard three-electrode one-compartment cell at room temperature. Steel AISI 316 sheets of approximately $1.0 \times 0.5$ $cm^2$ were used as support and working electrodes, while Pt sheets of the same area were used as counter electrode. The reference electrode was an Ag|AgCl electrode containing KCl saturated aqueous solution ($E^\circ=0.222$ V at 25° C.). A solution of terthiophene ($Th_3$) monomer (2 mM) was prepared in acetonitrile containing 0.1 M tetrabutylammonium tetrafluoroborate (TBATFB) as dopant agent. The cell was filled with 5 mL of the 2 mM $Th_3$ solution. Polymerization was carried out applying a constant potential of 1.0 V during a polymerization time of 0=150 seconds.

FIG. 17$a$ shows the FTIR spectrum of PTh$_3$. The most evident peaks in this range appeared as follows: the peak at that at 692 cm$^{-11}$ due to C—S—C ring deformation; the peak at 791 cm$^{-1}$ due to CH out-of-plane bending vibration ($\delta$ C—H) of 2,5-substituted thiophene rings; and the strong doublet-like band centered at 1260 cm$^{-1}$ and at 1050 cm$^{-1}$ due to the $\beta$ C—H bending in doped PTh$_3$ chains.

FIG. 17$b$ show the cyclic voltammograms recorded after 4, 12 and 24 h of E. Coli incubation as well as after 24 h of Cos-1 cells incubation. As it can be seen, the anodic peak associated to the NADH oxidation is clearly detected for E. coli after only 4 h, while this peak is barely perceptible for Cos-1 after 24 h. Again the invention is able to discriminate between the metabolisms of bacteria and eukaryotic cells.

With reference to FIG. 18, therein another embodiment to integrate PEDOT-based electrochemical sensors for detecting biofilms on implantable i-PP devices is illustrated. This new strategy, which consists on one functionalization and two polymerization steps (FIG. 18$a$) provides important advantages with respect to the simple mechanical pressing used in previous case to prepare i-PP/PEDOT.

A sketch of the three steps used to prepare the sensor integrated in an i-PP film typically used for biomedical prostheses is shown in FIG. 18$a$. The surface of the i-PP films was functionalized with low pressure radio-frequency (RF) oxygen plasma (80 MHz), using a LFG generator 1000 W, and a chamber of 25 dm$^3$. i-PP films of 6×5 cm$^2$ were placed inside the chamber, the system was purged up to 0.07 mbar of vacuum pressure and, subsequently, filled with oxygen plasma pressure of 0.30 mbar using a gas flow fixed during 180 seconds. The power discharge was of 250 W. After the plasma treatment, all functionalized i-PP films (i-PP$_f$) were stored under vacuum.

i-PP$_f$ films were cut in 0.5×1.5 cm$^2$ samples and a first layer of CP was adhered onto it by chemical oxidative polymerization. For this purpose, a i-PP$_f$ sample was immersed in 5 mL of 0.2 HCl with 50 mM hydroxymethyl-3,4-ethylenedioxythiophene (MHeDOT) monomer, which is 3,4-ethylenedioxythiophene derivative bearing a hydroxymethyl group to improve the solubility in water, during 30 min and under agitation (250 rpm). Then, 1 mL of 0.2 M HCl with 60 mM of ammonium persulfate (APS) was slowly dropped to the solution containing the monomer and the i-PP$_f$ film. The reaction, with a monomer: oxidant ratio of 1:1.2, was kept at 37° C. and 80 rpm. After 24 h, the resulting film, named i-PP$_f$/CP, was removed, washed and dried.

Finally, in the third step, a second CP layer was added to the i-PP$_f$/CP film. For this purpose, a i-PP$_f$/CP film, which was used as working electrode, was introduced in a three-electrode cell filled with 20 mL of an acetonitrile solution with 10 mM 3,4-ethylenedioxythiophene (EDOT) monomer and 0.1 M LiClO$_4$ as supporting electrolyte. A PEDOT layer was formed onto the PHMeDOT one by applying a constant potential of +1.40 V and adjusting the polymerization charge to +1.0 C. The aspect of the resulting electroactive i-PP film, hereafter named i-PP$_f$/CP$^2$ is compared in FIG. 18$b$ with those of i-PP, i-PP$_f$ and i-PP$_f$/CP$^2$. As is shown, the translucent aspect of pristine i-PP changes to whitish (i-PP$_f$), blueish (i-PP$_f$/CP) and dark blue (i-PP$_f$/CP$^2$), suggesting the success of the steps associated to the plasma functionalization, the incorporation of the PHMeDOT layer by oxidative polymerization, and the addition of the external PEDOT layer by anodic polymerization, respectively.

UV-Vis and FTIR spectra (FIGS. 19$a$ and 19$b$, respectively) definitively demonstrate the incorporation of PHMeDOT (1$^{st}$) and PEDOT (2$^{nd}$) layers to i-PP$_f$. As it was expected no absorption band was detected by UV-Vis spectroscopy for i-PP and i-PP$_f$. For i-PP$_f$/CP, the absorption in the range of 300-400 nm decreased, as is expected from the n-$\pi$ electronic transition of aromatic rings typically observed at ~250, and that in the range of 400-750 nm increased as corresponds to the polaron absorption of the doped PHMeDOT layer. This effect becomes more pronounced for i-PP$_f$/CP$^2$, suggesting that the doping level by the electrochemically polymerized PEDOT layer is higher than that of the internal PHMeDOT layer.

The FTIR spectrum of i-PP shows the characteristic absorption peaks with the broad and intense bands at 2918 cm$^{-1}$, the moderate absorption peaks associated to deformation vibration of the CH$_2$ group at 1455 cm$^{-1}$, and the methyl group vibrations at 1376 cm$^{-1}$. The absorption peaks at 841, 999 and 1167 cm$^{-1}$ are characteristic vibration of unsaturated CH$_2$ groups in i-PP. The FTIR spectrum of i-PP$_f$ shows some changes, new signals appearing at 1534 and 1686 cm$^{-1}$, which are attributed to C=O stretching, and a band at 1088 cm$^{-1}$ associated to C—O stretching. Detailed discussion of i-PP$_f$ spectrum was reported in recent work. Besides, PHMeDOT and PEDOT are revealed in the spectra of i-PP$_f$/CP and i-PP/CP$^2$ by the characteristic bands of the C—S and C—S—C vibrations in the thiophene ring at around 869, 757 and 614 cm$^{-1}$. However, many fingerprints of the CPs are FTIR spectra are hidden by the predominant bands of i-PP, which is main component. In order to overcome this issue, Raman spectra were recorded to visualize the presence of PHMeDOT and PEDOT.

Raman spectra of i-PP and i-PP$_f$, which are compared in FIG. 19$c$, shows that the latter peaks associated to crystalline i-PP (809 and 973 cm$^{-1}$) becomes enhanced after plasma treatment. In addition of the crystallinity increment, comparison between i-PP and i-PP$_f$ spectra reveals that plasma treatment induces a change in the shape and intensity of the band at 2962 cm$^{-1}$, which corresponds to the C—H stretching vibrations from methyl groups, as well as reduction of the CH$_3$ rocking band at 841 cm$^{-1}$. These features suggest that CH$_3$ are modified by the plasma, becoming the favorite site for the formation of oxidized groups, which is in agreement with previous work. Results displayed in FIG. 19$c$ show the predominance of CPs bands in the i-PP$_f$/CP and i-PP/CP$^2$ systems, which is due to the resonance Raman effect that increases the intensity of the bands of the material when the laser energy coincides with the frequency of the electronic transition of the sample.

FIG. 19$d$ compares the Raman spectra of i-PP/CP and i-PP/CP$^2$. Interestingly, the i-PP$_f$ band at 2962 cm$^{-1}$ is clearly detectable after the incorporation of the PHMeDOT layer, while it becomes hidden when the PEDOT is anodically polymerized. This feature suggests that the thickness of second CP layer in i-PP/CP$^2$ is much higher than the PHMeDOT one in i-PP/CP, as confirmed by profilometry measurements (see below). Furthermore, the spectra reported in FIG. 19$d$ exhibit the main characteristics peaks of PHMeDOT and PEDOT: C=C symmetrical stretching (1430 and 1420 cm$^{-1}$, respectively) and C=C asymmetrical stretching (1500 cm$^{-1}$).

Representative scanning electron microscopy (SEM) micrographs and atomic force microscopy (AFM) images of i-PP, i-PP$_f$/CP and i-PP/CP$^2$ are shown in FIG. 20. The i-PP surface film shows a flat and smooth morphology (FIG. 20$a$), which is modified after exposure to the oxygen plasma. Thus, plasma functionalization causes the apparition a superficial and homogeneous nano-patterning on the whole surface (FIG. 20b). This morphological change affects slightly to the topography, as is evidenced by comparing the 3D height AFM images of i-PP and i-PP$_f$. The surface roughness of i-PP, which is $R_q$=30±6 nm, increases to $R_q$=38±6 nm after plasma treatment.

The morphology of PHMeDOT in i-PP$_f$/CP is shown in FIG. 20c. SEM micrographs evidence that the oxidation polymerization of HMeDOT resulted in the formation of abundant and irregular PHMeDOT NPs between 100 and 200 nm in size. These NPs, which organized in a relatively compact layer of 1.1±0.1 μm in thickness, were randomly distributed on the i-PP$_f$ surface, forming a random contact network structure. However, the contact between such NPs is not large enough to ensure percolation and form conduction paths, as is demonstrated by the restricted electrochemical activity of i-PP$_f$/CP (see below). Besides, the oxidative polymerization step significantly enhanced the surface roughness of which increased from $R_q$=38±6 nm to $R_q$=312±12 nm.

Finally, PHMeDOT NPs were used as polymerization nuclei of PEDOT chains, which were electrochemically generated at a constant potential of 1.40 V. The morphology and topography of i-PP$_f$/CP$^2$ (FIG. 20d) are very similar to those reported for PEDOT films. Thus, anodically polymerized PEDOT organizes in clusters of aggregated molecules that are located at different levels. The roughness, $R_q$=611±57 nm, is about twice the i-PP$_f$/CP, indicating that PEDOT chains grow not only filling the empty spaces between neighboring PHMeDOT NPs (FIG. 20c) but also on the top of the layer. Indeed, PEDOT completely covers the PHMeDOT NPs, integrating them into a single conducting layer with continuous and well-defined conduction paths. This organization is clearly reflected in the 3D height AFM image (FIG. 20d), which shows the heterogeneous and porous topography of i-PP$_f$/CP$^2$ practically matches that found for PEDOT films. Consistently, the thickness of the conducting layer grows from 1.1±0.1 μm for i-PP$_f$/CP to 8.2±2.4 μm for i-PP$_f$/CP$^2$.

These morphological observations are consistent with the wettability of the different samples (FIG. 19e). Thus, contact angle (CA) measurements for water indicated that hydrophobic i-PP (CA=102°±3°) transforms into slightly hydrophilic i-PP$_f$ (CA=78°±5°) by oxygen plasma treatment due not only to the apparition of polar groups (e.g. C=O and C—O), as proved by FTIR spectroscopy, but also by the creation of a nano-patterning (FIG. 20b). Instead, the incorporation of PHMeDOT NPs did not increase the wettability, which has been attributed to the fact that the topographic changes experienced by i-PP$_f$/CP (CA=82°±3°) occurred at the submicrometric scale-length rather at the nanometric one. Finally, i-PP$_f$/CP$^2$ is very hydrophilic (CA<20°) because of the high doping level of electropolymerized PEDOT, which was found to accumulate about +0.5 positive charge per repeat unit when is obtained using identical experimental conditions to those applied in this work.

The electrochemical activity of the systems under study was investigated using phosphate buffer saline (PBS) solution, pH 7.4, as supporting electrolyte. Control voltammograms recorded for i-PP, i-PP$_f$ and i-PP$_f$/CP in PBS are compared in FIG. 21a. As expected, the electrochemical activity of i-PP and i-PP$_f$ are practically null (i.e. the areas of the voltammograms are negligible). However, the formation of PHMeDOT NPs on the surface of i-PP$_f$ results in an increment of electroactivity, even though the voltammogram recorded for i-PP$_f$ does not show oxidation nor reduction processes. This observation, which is consistent with the poor contact the CP NPs (FIG. 20c), indicates that formation of redox species in the potential range from −0.20 to 0.80 V is blocked by the i-PP$_f$ matrix.

The incorporation of a PEDOT layer using the PHMeDOT NPs as polymerization nuclei results in a huge increase of the electrochemical activity. The transformation associated to the formation of a dense and compact network of PEDOT chains filling the spaces between the NPs and coating them, as observed by SEM (FIG. 20d), is visually detected when the film progressively changes from blueish to dark blue with increasing polymerization charge (FIG. 21b). Inspection to the control voltammograms displayed in FIG. 21c shows that electroactivity of i-PP$_f$/CP is higher than that of i-PP$_f$/CP$^2$ by several orders of magnitude. More specifically, the voltammetric charge (Q) and the current density at the reversal potential ($j_{0.8}$) determined for i-PP/CP are Q=1.3·$10^{-5}$ C and $j_{0.8}$=3·$10^{-3}$ mA/cm$^{-2}$, while these parameters increases to Q=0.020 C $j_{0.8}$ mA/cm$^{-2}$ for i-PP/CP$^2$. This observation confirms that i-PP/CP$^2$ can be described as a network of PEDOT-based conduction paths coating the plasma treated i-PP film.

On the other hand, i-PP/CP$^2$ exhibits a very high electrochemical stability in PBS. FIG. 21c compares the first control voltammogram with that recorded after 50 consecutive oxidation-reduction cycles in the potential range from −0.20 to 0.80 V, both showing very similar anodic and cathodic areas. Indeed, the electrochemical activity of i-PP/CP$^2$ decreases by 1.1% only after 50 cycles. This is a very interesting observation since the electrochemical stability of PEDOT in PBS is known to be relatively low when the applied potential window is slightly wider. For example, the electrochemical activity of PEDOT films was reported to decrease by 17% and 39% when 10 and 50 redox cycles were applied in PBS using a potential range from −0.40 to 0.90 V.

The performance of the free-standing i-PP/CP$^2$ sensor probe towards the electrocatalytic oxidation of NADH from *E. coli* respiration reaction is proved in FIG. 22. Bacteria were cultured in Dulbecco's modified Eagle's medium (DMEM) supplemented with 2% fetal bovine serum (FBS; pH 8.1) and 0.2% NaHCO$_3$, as described above. As shown in FIG. 22, which compares the cyclic voltammograms recorded at different times (from 0 to 48 h separated by 12 h intervals), the oxidation of NADH to NAD+ is evidenced by oxidation peak at around 0.6 V. It is worth noting that the peak potential for NADH electro-oxidation shifted positively 170 mV after 48 h with respect to the initial measure (t=0), while the peak current density increased 1.88 mA/cm$^2$ (i.e. from 4.17 to 6.05 mA/cm$^2$). This has been attributed to successful selection of NADH as bacterial biomarker, which has been found to be permeable to bacteria membranes.

The invention claimed is:

1. A method for selective detection of infections, the method comprising detecting a concentration of nicotinamide adenine dinucleotide (NADH), from a bacterial culture through a cyclic voltammetry or chronoamperometry applied to an electrochemically active polymer, wherein the infections include at least a bacterial infection;

wherein the electrochemically active polymer comprises:

particles of amphiphilic copolymers consisting of a polythiophene backbone with grafted biocompatible polycaprolactone and polyethylene glycol blocks, or a layer of poly(hydroxymethyl-3,4-ethylenedioxythiophene) and a layer of poly(3,4-ethylenedioxythiophene), wherein the layer of poly(hydroxymethyl-3, 4-ethylenedioxythiophene) is deposited on top of a film of isotactic polypropylene and the layer of poly(3,4-ethylenedioxythiophene) is deposited on top of the layer of poly(hydroxymethyl-3,4-ethylenedioxythiophene).

2. The method according to claim 1, wherein the electrochemically active polymer further comprises polythiophenes substituted at the 3-position of the thiophene ring.

3. The method according to claim 1, wherein the electrochemically active polymer comprises particles of amphiphilic copolymers consisting of a polythiophene backbone with grafted biocompatible polycaprolactone and polyethylene glycol blocks, and the electrochemically active polymer is deposited on top of or integrated in a non-toxic and biocompatible substrate.

4. The method according to claim 3, wherein the non-toxic and biocompatible substrate is made of polypropylene, polyesters, polyamides, polycarbonates, vitreous carbon, hydroxyapatite or a metal including platinum, gold, stainless steel, titanium, or magnesium alloys.

5. A system for selective detection of infections, wherein the infections include at least a bacterial infection, the system comprising:

a medical device;

an electrochemical sensor including a solid substrate acting as a support, and an electrochemically active polymer deposited on top of said support and configured to be electrochemically activated, said electrochemical sensor, when in use, being adapted to be placed over a surface, part of the surface or in a body of said medical device; and a plurality of electrodes adapted and configured to apply an electrical potential to the electrochemically active polymer, wherein the medical device is configured to be located in a bacterial culture or located in a living tissue, and as a result of a cyclic voltammetry or chronoamperometry applied to the electrochemically active polymer, the electrochemically active polymer is configured to detect a concentration of nicotinamide adenine dinucleotide (NADH), and wherein the medical device comprises a suture, a surgical mesh, a vascular prosthesis, a hip prosthesis or a knee prosthesis wherein the electrochemically active polymer comprises:

particles of amphiphilic copolymers consisting of a polythiophene backbone with grafted biocompatible polycaprolactone and polyethylene glycol blocks, or a layer of poly(hydroxymethyl-3,4-ethylenedioxythiophene) and a layer of poly(3,4-ethylenedioxythiophene), wherein the layer of poly(hydroxymethyl-3,4-ethylenedioxythiophene) is deposited on top of the solid substrate and the layer of poly(3,4-ethylenedioxythiophene) is deposited on top of the layer of poly(hydroxymethyl-3,4-ethylenedioxythiophene), wherein the solid substrate is a film of isotactic polypropylene.

6. The system according to claim 5, wherein the plurality of electrodes includes screen printed electrodes (SPEs), or implantable electrodes.

7. The system according to claim 5, wherein the solid substrate is made of a non-toxic and biocompatible material including polypropylene, polyesters, polyamides, polycarbonates, vitreous carbon, hydroxyapatite or a metal including platinum, gold, stainless steel, titanium, or magnesium alloys.

8. The system according to claim 5, wherein the electrochemically active polymer comprises polythiophenes substituted at the 3-position of the thiophene ring.

9. The system according to claim 5, wherein:

the medical device comprises the surgical mesh, the vascular prosthesis, or the hip prosthesis; and the solid substrate includes a film, a mesh, a suture or a three-dimensional device.

\* \* \* \* \*